(12) United States Patent
Weyergang et al.

(10) Patent No.: US 11,506,668 B2
(45) Date of Patent: Nov. 22, 2022

(54) DIAGNOSIS AND TREATMENT OF CANCER

(71) Applicants: Olav Engebråten, Oslo (NO); Maria Eb Berstad, Oslo (NO); Kristian Berg, Heggedal (NO); Anette Weyergang, Oslo (NO)

(72) Inventors: Anette Weyergang, Oslo (NO); Maria Eb Berstad, Oslo (NO); Kristian Berg, Heggedal (NO); Olav Engebråten, Oslo (NO)

( * ) Notice: Subject to any disclaimer, the term of this patent is extended or adjusted under 35 U.S.C. 154(b) by 0 days.

(21) Appl. No.: 16/624,654

(22) PCT Filed: Jun. 22, 2018

(86) PCT No.: PCT/IB2018/000826
§ 371 (c)(1),
(2) Date: Dec. 19, 2019

(87) PCT Pub. No.: WO2018/234872
PCT Pub. Date: Dec. 27, 2018

(65) Prior Publication Data
US 2020/0182879 A1   Jun. 11, 2020

Related U.S. Application Data

(60) Provisional application No. 62/524,116, filed on Jun. 23, 2017.

(51) Int. Cl.
| | | |
|---|---|---|
| A61K 47/00 | (2006.01) | |
| G01N 33/00 | (2006.01) | |
| G01N 33/574 | (2006.01) | |
| A61K 47/68 | (2017.01) | |
| C07K 16/32 | (2006.01) | |
| A61K 45/06 | (2006.01) | |

(52) U.S. Cl.
CPC ... *G01N 33/57492* (2013.01); *A61K 47/6825* (2017.08); *A61K 47/6855* (2017.08); *C07K 16/32* (2013.01); *A61K 45/06* (2013.01); *C07K 2317/622* (2013.01); *C07K 2317/73* (2013.01); *C07K 2317/77* (2013.01)

(58) Field of Classification Search
CPC ......... G01N 33/57492; G01N 2800/52; G01N 33/57415; A61K 47/6825; A61K 47/6855; A61K 45/06; A61K 2039/505; C07K 16/32; C07K 2317/622; C07K 2317/73; C07K 2317/77; C07K 2319/55
See application file for complete search history.

(56) References Cited

U.S. PATENT DOCUMENTS

| | | |
|---|---|---|
| 2007/0128636 A1 | 6/2007 | Baker et al. |
| 2011/0044977 A1 | 2/2011 | Adler et al. |
| 2017/0037480 A1 | 2/2017 | Scherz-Shouval et al. |

FOREIGN PATENT DOCUMENTS

| | | |
|---|---|---|
| WO | WO 2009/146545 | 12/2009 |
| WO | 2014197937 | 12/2014 |

OTHER PUBLICATIONS

Frittoli et al (JCB 206:307-328, 2014), (Year: 2014).*
Mendoaz et al , J Cell Sci 126:3835-47, 2013 (Year: 2013).*
Zhao et al., Cancer Sci 101:1454-1462, 2010 (Year: 2010).*
Alberts, B. et al., Molecular Biology of the Cell, 4th edition, Chapter 13: Intracellular Vesicular Traffice, pp. 722-723.
Chavrier, P. et al., Localization of Low Molecular Weight GTP Binding Proteins to Exocytic and Endocytic Compartments, Cell, vol. 62, 317-329, Jul. 1990, pp. 317-329.
Baron, et al, *Journal of oncology pharmacy practice*, 2015, 21, 132-142.
Stenmark, *Nature reviews. Molecular cell biology*, 2009, 10, 513-525.
Baselga, et al, *Clinical cancer research*, 2016, 22, 3755-3763.
Sung-Bae Kim, Hans Wildiers, Ian E. Krop, Melanie Smitt, Ron Yu, Sanne Lysbet de Haas and Antonio Gonzalez-Martin, *Int J Cancer*, 2016, 139, 2336-2342.
K. Subik, J. F. Lee, L. Baxter, T. Strzepek, D. Costello, P. Crowley, L. Xing, M. C. Hung, T. Bonfiglio, D. G. Hicks and P. Tang, *Breast Cancer*(Auckl.). 2010, %20;4:35-41., 35-41.
R. L. Dillon, S. Chooniedass, A. Premsukh, G. P. Adams, J. Entwistle, G. C. MacDonald and J. Cizeau, *Journal of immunotherapy* (Hagerstown, Md. : 1997), 2016, 39, 117-126.
M. Zerial and H. McBride, *Nature reviews. Molecular cell biology*, 2001, 2, 107-117.
C. D. Austin, A. M. De Maziere, P. I. Pisacane, S. M. van Dijk, C. Eigenbrot, M. X. Sliwkowski, J. Klumperman and R. H. Scheller, *Molecular biology of the cell*, 2004, 15, 5268-5282.
E. A. Perez, S. A. Hurvitz, L. C. Amler, K. E. Mundt, V. Ng, E. Guardino and L. Gianni, *Breast cancer research : BCR*, 2014, 16, R50.
A. Citri, K. B. Skaria and Y. Yarden, *Experimental cell research*, 2003, 284, 54-65.
B. D. Grant and J. G. Donaldson, *Nature reviews. Molecular cell biology*, 2009, 10, 597-608.
E. Frittoli, A. Palamidessi, P. Marighetti, S. Confalonieri, F. Bianchi, C. Malinverno, G. Mazzarol, G. Viale, I. Martin-Padura, M. Garre, D. Parazzoli, V. Mattei, S. Cortellino, G. Bertalot, P. P. Di Fiore and G. Scita, *The Journal of cell biology*, 2014, 206, 307-328.
V. Bertelsen and E. Stang, *Membranes*, 2014, 4, 424-446.
K. Cortese, M. T. Howes, R. Lundmark, E. Tagliatti, P. Bagnato, A. Petrelli, M. Bono, H. T. McMahon, R. G. Parton and C. Tacchetti, *Molecular biology of the cell*, 2013, 24, 129-144.
S. Takahashi, K. Kubo, S. Waguri, A. Yabashi, H. W. Shin, Y. Katoh and K. Nakayama, *Journal of cell science*, 2012, 125, 4049-4057.
International Search Report and Written Opinion, Int'l Patent Application No. PCT/IB2018/000826, dated Nov. 16, 2018, 19 pages.
Eileen Edler et al. "Probing the druggability of membrane-bound Rab5 by molecular dynamics simulations" Journal of Enzyme Inhibition and Medicinal Chemistry, vol. 32, No. 1, Jan. 2017, pp. 434-443.

(Continued)

*Primary Examiner* — Lei Yao
(74) *Attorney, Agent, or Firm* — Pabst Patent Group LLP

(57) ABSTRACT

The present invention relates to compositions and methods for cancer therapy, including but not limited to, therapies that utilize cancer biomarkers. In particular, the present invention relates to compositions and methods for the prediction of a subject's response to cancer therapies.

14 Claims, 11 Drawing Sheets

(56) References Cited

OTHER PUBLICATIONS

Li, Y et al. "Expression of Rab5a correlates with tumor progression in pancreatic carcinoma" Virchows Archiv, vol. 470, No. 5, Feb. 2017, pp. 527-536.
Takamichi Igarashi et al. "Association of RAB5 overexpression in pancreatic cancer with cancer progression and poor prognosis via E-cadherin suppression" Oncotarget, vol. 8, No. 7, Feb. 2017, pp. 12290-12300.
Steven J. Wolf et al. "Intracellular trafficking as a determinant of AS-DACA cytotoxicity in rhabdomyosarcoma cells" BMC Cell Biology, vol. 12, No. 1, 2011, p. 36.
Min-Hao Yu et al. "Increased expression of Rab5A predicts metastasis and poor prognosis in colorectal cancer patients" International Journal of Clinical and Experimental Pathology, vol. 8, No. 6, 2015, pp. 6974-6980.
Hector Peinado et al. "Melanoma exosomes educate bone marrow progenitor cells toward a pro-metastatic phenotype through MET" Nature Medicine, vol. 18, No. 6, 2012, pp. 883-891.
Lixu Jin et al. "Down-regulation of Ras-related Protein Rab 5c-dependent Endocytosis and Glycolysis in Cisplatin-resistant Ovarian Cancer Cell Lines" Molecular & Cellular Proteomics, vol. 13, No. 11, 2014, pp. 3138-3151.
Y Pan et al. "MicroRNA-130a inhibits cell proliferation, invasion and migration in human breast cancer by targeting the RAB5A" International Journal of Clinical and Experimental Pathology, vol. 8, No. 1, 2015, pp. 384-393.
S D Da Silva et al. "Predominant Rab-GTPase amplicons contributing to oral squamous cell carcinoma progression to metastasis" Oncotarget, vol. 6, No. 26, 2015, pp. 21950-21963.
S Dutta et al. "Neuropilin-2 Regulates Endosome Maturation and EGFR Trafficking to Support Cancer Cell Pathobiology" Cancer Research, vol. 76, No. 2, 2016, pp. 418-428.
Allahyari, H. et al. "Immunotoxin: A new tool for cancer therapy" Tumor Biology, Feb. 2017, 1-11.
Peters, C. and Brown, S. "Antibody-drug conjugates as novel anti-cancer chemotherapeutics" Biosci. Rep. 2015, 35, e00225, 1-20.
Kim, E. and Kim, K. "Strategies and Advancement in Antibody-Drug Conjugate Optimization for Targeted Cancer Therapeutics" Biomolecules & Therapeutics, 23(6), 493-509, 2015.
Jose Baselga, Edith A. Perez, Tadeusz Pienkowski, Richard Bell, "Adjuvant Trastuzumab: A Milestone in the Treatment of HER-2-Positive Early Breast Cancer", The Oncologist 2006;11 (suppl 1):4-12.
Jose Baselga, "The EGFR as a target for anticancer therapy—focus on cetuximab", Jun. 25, 2001, European Journal of Cancer 37(2001) S16-S22.
Bente Bull-Hansen, Yu Cao, Kristian Berg, Ellen Skarpen, Michael G. Rosenblum, Anette Weyergang, "Photochemical activation of the recombinant HER2-targeted fusion toxin MH3-B1/rGel; Impact of HER2 expression on treatment outcome", Journal of Controlled Release 182 (2014) 58-66.
Yu Cao, James D. Marks, John W. Marks, Lawrence H. Cheung, Sehoon Kim, and Michael G. Rosenblum, "Construction and Characterization of Novel, Recombinant Immunotoxins Targeting the Her2/neu Oncogene Product: In vitro and In vivo Studies", Cancer Res 2009; 69: (23). Dec. 1, 2009.
Yu Cao, James D. Marks, Qian Huang, Stephen I. Rudnick, Chiyi Xiong, Walter N. Hittelman, Xiaoxia Wen, John W. Marks, Lawrence H. Cheung, Kim Boland, Chun Li, Gregory P. Adams, and Michael G. Rosenblum, "Single-Chain Antibody-Based Immunotoxins Targeting Her2/neu: Design Optimization and Impact of Affinity on Antitumor Efficacy and Off-Target Toxicity", Nov. 16, 2011; DOI: 10.1158/1535-7163.MCT-11-0519, Mol Cancer Ther; 11(1); 143-53.
Raphael A. Clynes, Terri L. Towers, Leonard G. Presta & Jeffrey V. Ravetch, "Inhibitory Fc receptors modulate in vivo cytoxicity against tumor targets", Nature Medicine • vol. 6 • No. 4 • Apr. 2000.

Hans K. Erickson, Peter U. Park, Wayne C. Widdison, Yelena V. Kovtun, Lisa M. Garrett, Karen Hoffman, Robert J. Lutz, Victor S. Goldmacher, and Walter A. Blattler, "Antibody-Maytansinoid Conjugates Are Activated in Targeted Cancer Cells by Lysosomal Degradation and Linker-Dependent Intracellular Processing", Cancer Res 2006; 66: (8). Apr. 15, 2006.
Armand De Gramont, Sarah Watson, Lee M. Ellis, Jordi Rodón, Josep Tabernero, Aimery de Gramont and Stanley R. Hamilton, "Pragmatic issues in biomarker evaluation for targeted therapies in cancer", Nat. Rev. Clin. Oncol. 12, 197-212 (2015); published online Nov. 25, 2014.
Nadia Harbeck, Matthias W. Beckmann, Achim Rody, Andreas Schneeweiss, Volkmar Müller, Tanja Fehm, Norbert Marschner, Oleg Gluz, Iris Schrader, Georg Heinrich, Michael Untch, Christian Jackisch, "HER2 Dimerization Inhibitor Pertuzumab—Mode of Action and Clinical Data in Breast Cancer", Breast Care 2013;8:49-55.
Abraham Hernandez-Blanquisett, Diego Touya, Kathrin Strasser-Weippl, Rossana Ruiz, Jessica St. Louis, Paul Goss, "Current and emerging therapies of HER2-positive metastatic breast cancer", The Breast 29 (2016) 170e177.
Maria Teresa Martinez, José Alejandro Pérez-Fidalgo, Paloma Martín-Martorell, Juan Miguel Cejalvo, Vanesa Pons, Begona Bermejo, Miguel Martín, Joan Albanell, Ana Lluch, "Treatment of HER2 positive advanced breast cancer with T-DM1: A review of the literature", Critical Reviews in Oncology/Hematology 97 (2016) 96-106.
Gail D. Lewis Phillips, Guangmin Li, Debra L. Dugger, Lisa M. Crocker, Kathryn L. Parsons, Elaine Mai, Walter A. Blattler, John M. Lambert, Ravi V.J. Chari, Robert J. Lutz, Wai Lee T. Wong, Frederic S. Jacobson, Hartmut Koeppen, Ralph H. Schwall, Sara R. Kenkare-Mitra, Susan D. Spencer, and Mark X. Sliwkowski, "Targeting HER2-Positive Breast Cancer with Trastuzumab-DM1, an Antibody-Cytotoxic Drug Conjugate", Cancer Res 2008; 68: (22). Nov. 15, 2008.
Mothaffar F. Rimawi, Rachel Schiff, and C. Kent Osborne, "Targeting HER2 for the Treatment of Breast Cancer", Annu. Rev. Med. 2015. 66:111-28.
Michael Ritchie, Lioudmila Tchistiakova and Nathan Scott, "Implications of receptor-mediated endocytosis and intracellular trafficking dynamics in the development of antibody drug conjugates", mAbs 5:1, 13-21; Jan./Feb. 2013; © 2013 Landes Bioscience.
Michael G. Rosenblum, William A. Kohr, Kenneth L. Beattie, Wanda G. Beattie, William Marks, P. David Toman, and Lawrence Cheung, "Amino Acid Sequence Analysis, Gene Construction, Cloning, and Expression of Gelonin, a Toxin Derived from Gelonium multiflorum", Journal of Interferon and Cytokine Research 15:547-555 (1995).
Dennis J. Slamon, William Godolphin, Lovell A. Jones, John A Holt, Steven G. Wong, Duane E. KE11H, Wendy J. Levin, Susan G. Stuart, Judy Udove, AxEL Ullrich, Michael F. Press, "Studies of the HER-2/neu Proto-oncogene in Human Breast and Ovarian Cancer", Science; May 12, 1989; 244, 4905.
Fiorenzo Stirpe, Sjur Olsnes, and Alexander Pihl, "Gelonin, a New Inhibitor of Protein Synthesis, Nontoxic to Intact Cells", The Journal of Biological Chemistry, vol. 255, No. 14, issue of Jul. 25, pp. 6947-6953, 1980.
Sunil Verma, M.D., David Miles, M.D., Luca Gianni, M.D., Ian E. Krop, M.D., Ph.D., Manfred Welslau, M.D., José Baselga, M.D., Ph.D., Mark Pegram, M.D., Do-Youn Oh, M.D., Ph.D., Véronique Diéras, M.D., Ellie Guardino, M.D., Ph.D., Liang Fang, Ph.D., Michael W. Lu, Pharm.D., Steven Olsen, M.D., Ph.D., Kim Blackwell, M.D., "Trastuzumab Emtansine for HER2-Positive Advanced Breast Cancer", N Engl J Med. Nov. 8, 2012; 367(19): 1783-1791. doi:10.1056/NEJMoa1209124.
Anette Weyergang, På l Kristian Selbo, Kristian Berg, "Photochemically stimulated drug delivery increases the cytotoxicity and specificity of EGF-saporin", Journal of Controlled Release 111 (2006) 165-173.
Birte Sonnichsen, Stefano De Renzis, Erik Nielsen, Jens Rietdorf, and Marino Zerial, "Distinct Membrane Domains on Endosomes in the Recycling Pathway Visualized by Multicolor Imaging of Rab4, Rab5, and Rab11", The Journal of Cell Biology, vol. 149, No. 4, May 15, 2000 901-913.

(56) References Cited

OTHER PUBLICATIONS

Mona Wilcke, Ludger Johannes, Thierry Galli, Véronique Mayau, Bruno Goud, and Jean Salamero, "Rab11 Regulates the Compartmentalization of Early Endosomes Required for Efficient Transport from Early Endosomes to the trans-Golgi Network", The Journal of Cell Biology, vol. 151, No. 6, Dec. 11, 2000 1207-1220.

Database UniProt [Online] Feb. 1, 1991, "RecName: Full-Ras-related Rab-5A;", retrived from EBI accession No. UNIPROT:P20339.

Millino, et al., "Gene and MicroRNA Expression Are Predictive of Tumor Response in Rectal Adenocarcinoma Patients Treated With Preoperative Chemoradiotherapy", Journal of Cellular Physiology, 232(2):426-435 (2017).

* cited by examiner

FIG. 2B
FIG. 2C
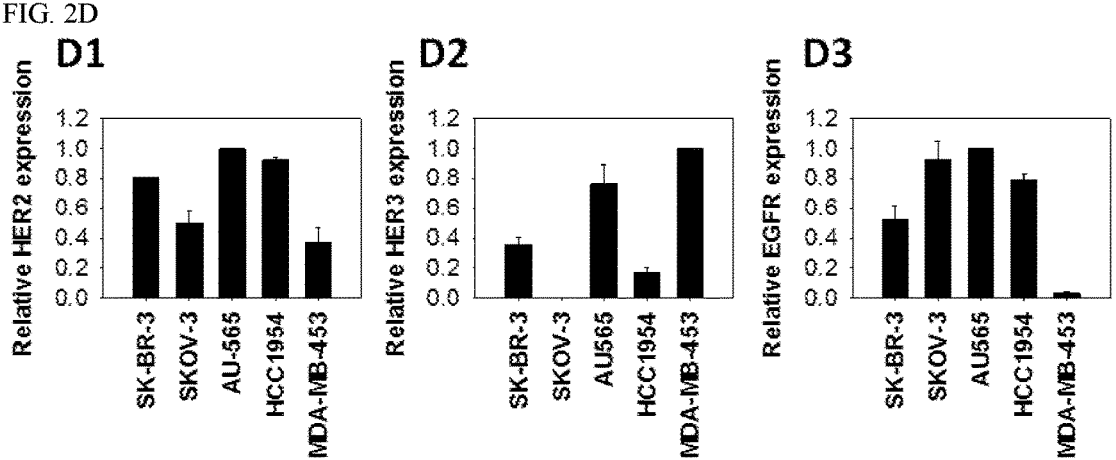
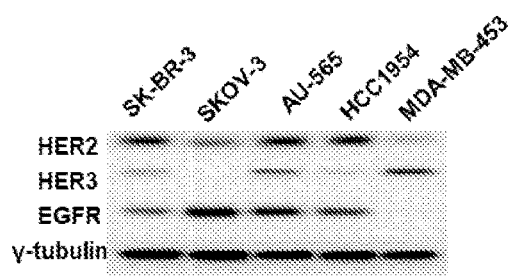
FIG. 2D
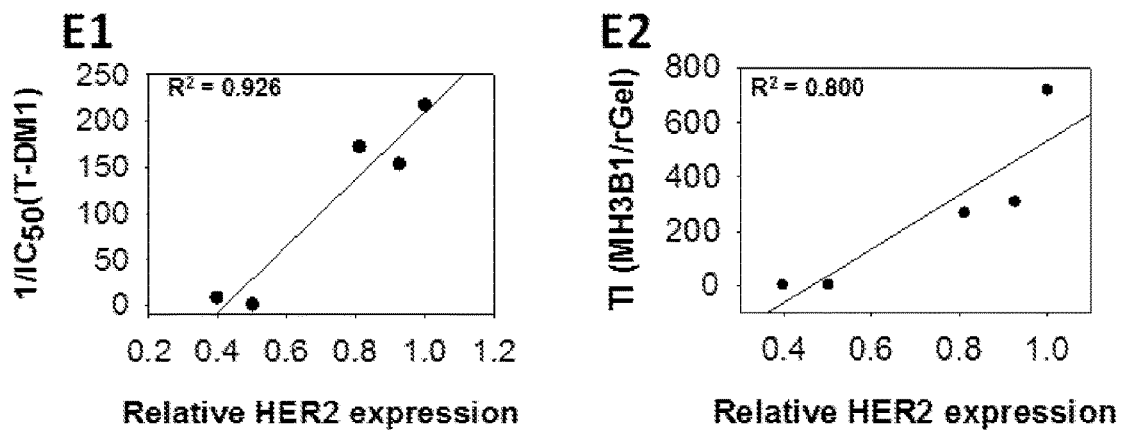
FIG. 2E

Regression charts between T-DM1 response and levels of HER2, HER3 and EGFR

Regression charts between MH3-B1/rGel response and levels of HER2, HER3 and EGFR

DIAGNOSIS AND TREATMENT OF CANCER

CROSS REFERENCE TO RELATED APPLICATIONS

This application is a Section 371 U.S. national stage entry of International Patent Application No. PCT/IB2018/000826, International Filing Date Jun. 22, 2018, which claims the benefit of U.S. Provisional Application Ser. No. 62/524,116, filed Jun. 23, 2017 which are incorporated herein by reference in their entireties.

FIELD OF THE INVENTION

The present invention relates to compositions and methods for cancer diagnosis, research and therapy, including but not limited to, cancer markers. In particular, the present invention relates to compositions and methods for the prediction of a subject's response to cancer therapies.

BACKGROUND OF THE INVENTION

The increased focus on personalized medicine has together with our increasing knowledge on cancer biology revealed the high potential of biomarkers in cancer treatment. A specter of different biomarkers is already incorporated in clinical practice to predict patient survival, evaluate therapeutic efficacy or monitor disease progression (Bailey et al, *Discovery medicine*, 2014, 17:101-114). The high cost of targeted cancer therapeutics is a strong driver for development of biomarkers in order to select those patients who are most likely to benefit from the treatment. To this end, regulatory authorities increasingly require inclusion of predictive biomarkers for new therapies under clinical evaluation (Marton & Weiner, *Biomed Res Int* 2013; 2013:891391.

Breast cancer is the second most common form of cancer among women in the U.S., and the second leading cause of cancer deaths among women. While the 1980s saw a sharp rise in the number of new cases of breast cancer, that number now appears to have stabilized. The drop in the death rate from breast cancer is probably due to the fact that more women are having mammograms. When detected early, the chances for successful treatment of breast cancer are much improved.

Breast cancer, which is treated by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these are currently known to affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy.

Prognosis is influenced by the age of the patient, stage of the disease, pathologic characteristics of the primary tumor including the presence of tumor necrosis, estrogen-receptor (ER) and progesterone-receptor (PR) levels in the tumor tissue, HER2 overexpression status and measures of proliferative capacity, as well as by menopausal status and general health. Overweight patients may have a poorer prognosis (Bastarrachea et al., Annals of Internal Medicine, 120: 18 [1994]). Prognosis may also vary by race, with blacks, and to a lesser extent Hispanics, having a poorer prognosis than whites (Elledge et al., Journal of the National Cancer Institute 86: 705 [1994]; Edwards et al., Journal of Clinical Oncology 16: 2693 [1998]).

The three major treatments for breast cancer are surgery, radiation, and drug therapy. No treatment fits every patient, and often two or more are required. The choice is determined by many factors, including the age of the patient and her menopausal status, the type of cancer (e.g., ductal vs. lobular), its stage, whether the tumor is hormone-receptive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are wide spread. Drug therapies include classic chemotherapy drugs, hormone blocking treatment (e.g., aromatase inhibitors, selective estrogen receptor modulators, and estrogen receptor downregulators), and monoclonal antibody treatment (e.g., against HER2). They may be used separately or, most often, in different combinations.

HER2 (ERBB2) is a validated biomarker in breast cancer and HER2 gene amplification or protein over-expression is found in ~20% of newly diagnosed breast cancer patients (Slamon, et al., *Science*, 1989, 244, 707-712; Hernandez-Blanquisett, et al, *Breast (Edinburgh, Scotland)*, 2016, 29, 170-177). HER2 is utilized as a therapeutic biomarker for treatment with HER2-targeting monoclonal antibodies (mAbs) (trastuzumab and pertuzumab) and tyrosine kinase inhibitors (TKIs) (lapatinib and afatinib) (Hernandez-Blanquisett, et al, *Breast (Edinburgh, Scotland)*, 2016, 29, 170-177). The pharmacological effects of HER2-targeted mAbs and TKIs are a direct consequence of drug-target interaction and include antibody-mediated cellular cytotoxicity (ADCC) (mAbs), HER2 down regulation and inhibition of growth promoting signaling (Rimawi, et al, *Annual review of medicine*, 2015, 66, 111-128; Clynes, et al, *Nature medicine*, 2000, 6, 443-446; Harbeck, et al, *Breast care*, 2013, 8, 49-55). The ability of HER2 to undergo receptor-mediated endocytosis also makes this transmembrane protein a candidate for delivery of cytotoxic agents into the cancer cells. This has indeed been exemplified by the antibody-drug conjugate (ADC) trastuzumab emtasine (T-DM1) (Lewis Phillips, et al, *Cancer research*, 2008, 68, 9280-9290; Verma, et al, *The New England journal of medicine*, 2012, 367, 1783-1791; Barok, et al, *Breast cancer research*, 2011, 13, R46) which received FDA approval for treatment of metastatic breast cancer in 2013.

T-DM1 consists of trastuzumab linked by a thioether (N-maleimidomethyl cyclohexane-1-carboxylate (MCC)) to the highly cytotoxic maytansine-derived drug, DM-1 (Baron, et al, *Journal of oncology pharmacy practice*, 2015, 21, 132-142). Upon administration, T-DM1 binds to HER2 and is taken into the cell by HER2-mediated endocytosis. Proteolytic degradation of the trastuzumab-component within the endo/lysosomal pathway is postulated as the mechanism for cytosolic release of DM1 which subsequently induces microtubule destabilization and cell death (Erickson, et al, *Cancer research*, 2006, 66, 4426-4433; Martinez, et al, *Critical reviews in oncology/hematology*, 2016, 97, 96-106). T-DM1 therefore induces a cytotoxic mechanism of action within the cell in addition to the pharmacological effects generated by its trastuzumab-component.

Another, yet experimental, approach to utilize HER2 as a drug-transporter is through the use of HER2-targeted fusion toxins, such as MH3-B1/rGel, consisting of the HER2- binding single chain variable fragment MH3-B1 genetically fused to the type I ribosome-inactivating protein toxin gelonin (Cao, et al, *Cancer Res.*, 2009, 69, 8987-8995; Cao, et al, *Mol. Cancer Ther.*, 2012, 11, 143-153). MH3-B1/rGel is taken up through HER2-mediated endocytosis and is subsequently released into the cytosol where it binds to the ribosomes and inhibit translation (Stirpe, et al, *J Biol. Chem.*, 1980, 255, 6947-6953). MH3-B1/rGel therefore also induces a cytotoxic effect inside the cell in addition to its binding effects on HER2.

The mechanisms of HER2-binding drugs with intracellular action points are clearly more complex compared to HER2-targeting mAbs and TKIs and this should be reflected in the biomarkers used to predict drug-response (Ritchie, et al, mAbs, 2013, 5, 13-21). Evaluation of biomarkers for T-DM1 efficacy have, however, been focused on HER2 and its downstream signaling in addition to HER3 (Baselga, et al, *Clinical cancer research*, 2016, 22, 3755-3763; Kim, et al, *Int J Cancer*, 2016, 139, 2336-2342), and little is known on the impact of proteins involved in endocytosis, endocytic vesicle transport and exocytosis. There is a need for additional biomarkers to improve the predictive value of antibody drug conjugates and immunotoxins targeted to HER2 and other targeting receptors. The present study was aimed at evaluating proteins in the Rab GTPase family (Stenmark, *Nature reviews. Molecular cell biology*, 2009, 10, 513-525) as well as proteins specifically involved in HER2 endocytosis as possible biomarkers for the therapeutic effect of HER2-targeting ADCs and immunotoxins.

SUMMARY OF THE INVENTION

The present invention relates to compositions and methods for cancer therapy, including but not limited to, therapies that utilize cancer biomarkers. In particular, the present invention relates to compositions and methods for the prediction of a subject's response to cancer therapies.

Targeted therapeutics strongly depend on validated biomarkers in order to select those patients most likely to benefit from the treatment. HER2 already serves as a therapeutic biomarker for several tyrosine kinase inhibitors (TKIs) and monoclonal antibodies (mAbs) directed against HER2. HER2 may, however, also be utilized as a transport gate in order to deliver cytotoxic agents into the cell cytosol, such as by HER2-targeted antibody drug conjugates (ADCs) and antibody toxin conjugates (immunotoxins). The therapeutic biomarkers for such drugs may be more complex compared to biomarkers for TKIs and mAbs since they, in addition to the biomarker acting as a target, may reflect mechanisms of drug uptake and intracellular action.

A panel of HER2-positive breast and ovarian cancer cell lines was in the present study evaluated with respect to sensitivity towards the two HER2-targeted drugs; the ADC trastuzumab-emtansine (T-DM1) and the antibody toxin conjugate MH3-B1/rGel. The drug sensitivity was correlated to the expression level of HER2 in combination with HER3 and EGFR, which may impact on the pharmacology of the targeting moieties of the drugs, as well as Rab4, Rab5, Rab11 and HSP90 involved in endocytic trafficking, with possible impact on the pharmacology of the toxic moieties. The early endosome marker Rab5 and early recycling marker Rab4 were indicated as possible therapeutic biomarkers for both T-DM1 and MH3-B1/rGel. Toxicity of MH3-B1/rGel was, in addition, shown to be dependent on HSP90 and Rab11 (inverse). The present results outline, for the first time, proteins involved in endocytic trafficking as possible biomarkers for HER2-targeted ADCs and antibody toxin conjugates as well as ADCs and targeted antibody toxin conjugates in general. In addition, a mathematical approach is provided to validate combinations of biomarkers with diverse contribution factors.

Accordingly, in some embodiments, the present invention provides a method for treating a patient diagnosed with cancer with an antibody drug conjugate or an antibody toxin conjugate, comprising: a) determining the normalized protein expression level of the receptor of the antibody component of the antibody drug or toxin conjugate and at least one additional protein marker selected from Rab5, Rab4, Rab11 and HSP90 in a biological sample from said patient; b) generating a compound expression index of the level of protein expression of the receptor and the marker; and c) treating the patient with said antibody drug or toxin conjugate based on the compound expression index. In some embodiments, the receptor is HER2, HER3 or EGFR.

In some embodiments, the method comprises administering the antibody drug conjugate or antibody toxin conjugate when an expression index of an increased level of protein expression of HER2 in addition to RAB5 is determined. In some embodiments, the method comprises administering the antibody drug conjugate or antibody toxin conjugate when an expression index of an increased level of protein expression of HER2 in addition to Rab5 and Rab4 is determined. In some embodiments, the method comprises administering the antibody drug conjugate or antibody toxin conjugate when an expression index of an increased level of protein expression of HER2 in addition to Rab5 and Rab4 is determined. In some embodiments, the method comprises administering the antibody drug conjugate or antibody toxin conjugate when an expression index of an increased level of protein expression of HER2 in addition to RAB5, RAB4 and HSP90 is determined.

In some embodiments, the biological sample from said patient is a surgical tumor sample, a biopsy sample or a blood sample. In some embodiments, the cancer is breast cancer, colorectal cancer, lung cancer, prostate cancer, melanoma, glioblastoma, pancreatic cancer, renal cell carcinoma, ovarian cancer, bladder cancer, gastrointestinal cancer, mesothelioma, multiple myeloma, acute myelogenous leukemia, acute lymphoblastic leukemia, and Non-Hodgkin's Lymphoma.

In some embodiments, the antibody drug conjugate is Trastuzumab emtansine (T-DM1, Kadcyla), Brentuximab vedotin (SGN-35), Inotuzumab ozogamicin (CMC-544), Pinatuzumab vedotin (RG-7593), Polatuzumab vedotin (RG-7596), Lifastuzumab vedotin (DNIB0600A, RG-7599), Glembatuzumab vedotin (CDX-011), Coltuximab ravtansine (SAR3419), Lorvotuzumab mertansine (IMGN-901), Indatuximab ravtansine (BT-062), Sacitizumab govitican (IMMU-132), Labetuzumab govitican (IMMU-130), Milatuzumab doxorubicin (IMMU-110), Indusatumab vedotin (MLN-0264), Vadastuximab talirine (SGN-CD33A), Denintuzumab mafodotin (SGN-CD19A), Enfortumab vedotin (ASG-22ME), Rovalpituzumab tesirine (SC16LD6.5), Vandortuzumab vedotin (DSTP3086S, RG7450), Mirvetuximab soravtansine (IMGN853), ABT-414, IMGN289, or AMG595.

In some embodiments, the antibody toxin conjugate is MH3-B1/rGel, denileukin diftitox (DAB389IL2), moxetumomab pasudotox (CAT-8015), oportuzumab monotox (VB4-845), Resimmune, LMB-2, DT2219ARL, HuM195/rGel, RG7787, MOC31PE or D2C7-IT. In some embodiments, the determining comprises an immunoassay.

Further embodiments provide a method of determining a treatment course of action, comprising, comprising: a) determining the normalized protein expression level of the receptor of the antibody component of the antibody drug conjugate or antibody toxin conjugate and at least one additional marker selected from RAB5, RAB4, RAB11 and HSP90 in a biological sample from said patient; b) generating a compound expression index of the level of protein expression of the receptor and the marker; and c) recommending a treatment course of action based on the compound expression index.

Additional embodiments provide a method for determining a compound expression index in a biological sample from a patient diagnosed with cancer, comprising: a) determining the normalized protein expression level of the ligand of the antibody component of an antibody drug conjugate or antibody toxin conjugate and at least one additional marker selected from, for example, RAB5, RAB4, RAB11 and HSP90 in a biological sample from the patient; and b) generating a compound expression index of the level of protein expression of the ligand and the marker.

Yet other embodiments provide a kit, comprising: at least one first reagent for detection of the protein expression level at least one first marker selected, for example HER2, HER3, and EGFR and at least one second reagent for detection of an expression level of at least one second marker selected from, for example RAB5, RAB4, RAB11 or HSP90. In some embodiments, the reagents are antibodies.

Still further embodiments provide a system, comprising: a) at least one first reagent for detection of an expression level of at least one first marker selected, for example HER2, HER3, and EGFR and at least one second reagent for detection of an expression level of at least one second marker selected from, for example RAB5, RAB4, RAB11 or HSP90; and b) a computer processor and computer software for calculating a compound expression index based on the expression levels.

In still other embodiments, the present invention provides methods of treating cancer in a patient comprising: obtaining a sample comprising cancer cells from the patient; measuring the expression level of RAB5 in the cancer cells by an in vitro assay; and administering an effective amount of an immunoconjugate targeting a surface antigen of the cancer cells if the expression level of RAB5 in the cancer cell sample is increased as compared to a predetermined reference level; or administering an antigen binding protein that does not comprise a drug or toxin if the expression level of RAB5 in the cancer cell sample is decreased as compared to the predetermined reference level.

In some preferred embodiments, measuring the expression level of RAB5 in the cancer cells comprises measuring the level of RAB5 mRNA. In some preferred embodiments, measuring the expression level of RAB5 in the cancer cells comprises measuring the level of RAB5 protein. In some preferred embodiments, the RAB5 is RAB5A. In some preferred embodiments, the RAB5 is RAB5B. In some preferred embodiments, the RAB5 is RAB5C.

In some preferred embodiments, the methods further comprise the step of assaying the expression level of one or more of RAB4, RAB11 or HSP90. In some preferred embodiments, the methods further comprise the steps of incorporating the expression level of one or more of RAB4, RAB11 or HSP90 into an expression index with the RAB5 expression level and administering the effective amount of an immunoconjugate targeting a surface antigen of the cancer cells if the expression index is increased as compared to predetermined reference level.

In some preferred embodiments, the cancer cells are obtained from a surgical tumor sample, a biopsy sample or a blood sample.

In some preferred embodiments, the immunoconjugate binds to an antigen selected from the group consisting of HER2, HER3, EGFR, CD3ε, CD19, CD22, CD25, CD30, CD33, CD56, CEA (CD66e), CD74, CD79a, CD138, NaPi2b, gpNMB, TROP-2, GUCY2C, Nectin-4, SC-16, STEAP1, FRα, IL-2R, EpCAM, and MSLN. In some preferred embodiments, the immunoconjugate is an antibody drug conjugate is selected from the group consisting of trastuzumab emtansine, brentuximab vedotin, inotuzumab ozogamicin, pinatuzumab vedotin, polatuzumab vedotin, lifastuzumab vedotin, glembatuzumab vedotin, coltuximab ravtansine), lorvotuzumab mertansine, indatuximab ravtansine, sacituzumab govitican, labetuzumab govitican, milatuzumab doxorubicin, indusatumab vedotin, vadastuximab talirine, denintuzumab mafodotin, enfortumab vedotin, rovalpituzumab tesirine, vandortuzumab vedotin, mirvetuximab soravtansine, ABT-414, IMGN289, and AMG595. In some preferred embodiments, the immunoconjugate is an immunotoxin is selected from the group consisting of MH3-B1/rGel, denileukin diftitox, moxetumomab pasudotox, oportuzumab monotox, resimmune, LMB-2, DT2219ARL, HuM195/rGel, RG7787, MOC31PE and D2C7-IT.

In some preferred embodiments, the cancer cells are selected from the group consisting of breast cancer cells, colorectal cancer cells, lung cancer cells, prostate cancer cells, melanoma cells, glioblastoma cells, pancreatic cancer cells, renal cell carcinoma cells, ovarian cancer cells, bladder cancer cells, endometrial cancer cells, gastrointestinal cancer cells, mesothelioma cells, multiple myeloma cells, acute myelogenous leukemia cells, acute lymphoblastic leukemia cells, and Non-Hodgkin's Lymphoma.

In some preferred embodiments, the methods further comprise the step of assaying the expression of the surface antigen on the cancer cells.

In some particularly preferred embodiments, the cancer cells are breast cancer cells. In some preferred embodiments, the surface antigen is selected from the group consisting of at least one of Epidermal Growth Factor Receptor (HER1), HER2, HER3 and combinations thereof and the immunoconjugate is targeted to said surface antigen. In some preferred embodiments, the antibody drug conjugate or immunotoxin is selected from the group consisting of Trastuzumab emtansine (T-DM1), ABT-414, IMGN289, AMG595, and AMG595. In some preferred embodiments, the surface antigen is HER2. In some preferred embodiments, the immunoconjugate is Trastuzumab emtansine (T-DM1).

In some preferred embodiments, the present invention provides an immunoconjugate targeting a surface antigen for use in a method for the treatment of cancer in a patient wherein cancer cells from said patient express said antigen and exhibit an increased expression level of RAB5 as assayed by an in vitro expression assay as compared to a predetermined reference level. In other preferred embodiments, the present invention provides an antigen binding protein that is not conjugated to a drug or toxin for use in a method for the treatment of cancer in a patient wherein cancer cells from said patient express said antigen and exhibit an decreased expression level of RAB5 as assayed by an in vitro expression assay as compared to a predetermined reference level.

In some preferred embodiments, the in vitro expression assay is a RAB5 mRNA assay. In some preferred embodiments, the in vitro expression assay is a RAB5 protein assay.

In some preferred embodiments, the RAB5 is RAB5A. In some preferred embodiments, the RAB5 is RAB5B. In some preferred embodiments, the RAB5 is RAB5C.

In some preferred embodiments, the immunoconjugate binds to an antigen selected from the group consisting of HER2, HER3, EGFR, CD3ε, CD19, CD22, CD25, CD30, CD33, CD56, CEA (CD66e), CD74, CD79a, CD138, NaPi2b, gpNMB, TROP-2, GUCY2C, Nectin-4, SC-16, STEAP1, FRα, IL-2R, EpCAM, and MSLN. In some preferred embodiments, the immunoconjugate is an antibody drug conjugate is selected from the group consisting of trastuzumab emtansine, brentuximab vedotin, inotuzumab ozogamicin, pinatuzumab vedotin, polatuzumab vedotin, lifastuzumab vedotin, glembatuzumab vedotin, coltuximab ravtansine), lorvotuzumab mertansine, indatuximab ravtansine, sacitizumab govitican, labetuzumab govitican, milatuzumab doxorubicin, indusatumab vedotin, vadastuximab talirine, denintuzumab mafodotin, enfortumab vedotin, rovalpituzumab tesirine, vandortuzumab vedotin, mirvetuximab soravtansine, ABT-414, IMGN289, and AMG595. In some preferred embodiments, the immunoconjugate is an immunotoxin is selected from the group consisting of MH3-B1/rGel, denileukin diftitox, moxetumomab pasudotox, oportuzumab monotox, resimmune, LMB-2, DT2219ARL, HuM195/rGel, RG7787, MOC31PE and D2C7-IT.

In some preferred embodiments, the cancer cells are selected from the group consisting of breast cancer cells, colorectal cancer cells, lung cancer cells, prostate cancer cells, melanoma cells, glioblastoma cells, pancreatic cancer cells, renal cell carcinoma cells, ovarian cancer cells, bladder cancer cells, endometrial cancer cells, gastrointestinal cancer cells, mesothelioma cells, multiple myeloma cells, acute myelogenous leukemia cells, acute lymphoblastic leukemia cells, and Non-Hodgkin's Lymphoma.

In some preferred embodiments, the cancer cells are breast cancer cells. In some preferred embodiments, the surface antigen is selected from the group consisting of at least one of Epidermal Growth Factor Receptor (HER1), HER2, HER3 and combinations thereof and the antibody drug conjugate or immunotoxin is targeted to said surface antigen. In some preferred embodiments, the antibody drug conjugate or immunotoxin is selected from the group consisting of Trastuzumab emtansine (T-DM1), ABT-414, IMGN289, AMG595, and AMG595. In some preferred embodiments, the surface antigen is HER2. In some preferred embodiments, the immunoconjugate is Trastuzumab emtansine (T-DM1).

In still further preferred embodiments, the present invention provides in vitro methods for determining whether a human cancer cell is responsive to immunoconjugates targeting surface antigens on the cancer cell comprising: obtaining a sample comprising cancer cells from a patient; and measuring the expression level of RAB5 in the cancer cells by an in vitro assay, wherein an increased level of RAB5 expression as compared to a predetermined reference level is indicative of responsiveness to said immunoconjugate.

In some preferred embodiments, the in vitro expression assay is a RAB5 mRNA assay. In some preferred embodiments, the in vitro expression assay is a RAB5 protein assay. In some preferred embodiments, the RAB5 is RAB5A. In some preferred embodiments, the RAB5 is RAB5B. In some preferred embodiments, the RAB5 is RAB5C. In some preferred embodiments, the methods further comprise the step of assaying the expression level of one or more of RAB4, RAB11 or HSP90. In some preferred embodiments, the methods further comprise the steps of incorporating the expression level of one or more of RAB4, RAB11 or HSP90 into an expression index with the RAB5 expression level.

In some preferred embodiments, the cancer cells are obtained from a surgical tumor sample, a biopsy sample or a blood sample. In some preferred embodiments, the cancer cells are selected from the group consisting of breast cancer cells, colorectal cancer cells, lung cancer cells, prostate cancer cells, melanoma cells, glioblastoma cells, pancreatic cancer cells, renal cell carcinoma cells, ovarian cancer cells, bladder cancer cells, endometrial cancer cells, gastrointestinal cancer cells, mesothelioma cells, multiple myeloma cells, acute myelogenous leukemia cells, acute lymphoblastic leukemia cells, and Non-Hodgkin's Lymphoma.

In some preferred embodiments, the cancer cells are breast cancer cells. In some preferred embodiments, the methods further comprise the step of assaying the expression of the surface antigen on the cancer cells. In some preferred embodiments, the surface antigen is selected from the group consisting of at least one of Epidermal Growth Factor Receptor (HER1), HER2, HER3 and combinations thereof and the antibody drug conjugate or immunotoxin is targeted to one of Epidermal Growth Factor Receptor (HER1), HER2, and HER3. In some particularly preferred embodiments, the surface antigen is HER2.

In some preferred embodiments, the methods further comprise the step of administering an immunoconjugate to the subject when the expression level of RAB5 is increased as compared to a reference RAB5 expression level.

In some preferred embodiments, the methods further comprise the step of administering an antibody that does not comprise a drug or toxin to the subject when the expression level of RAB5 is decreased as compared to a reference RAB5 expression level.

Additional embodiments are described herein.

DEFINITIONS

Figure 1A:
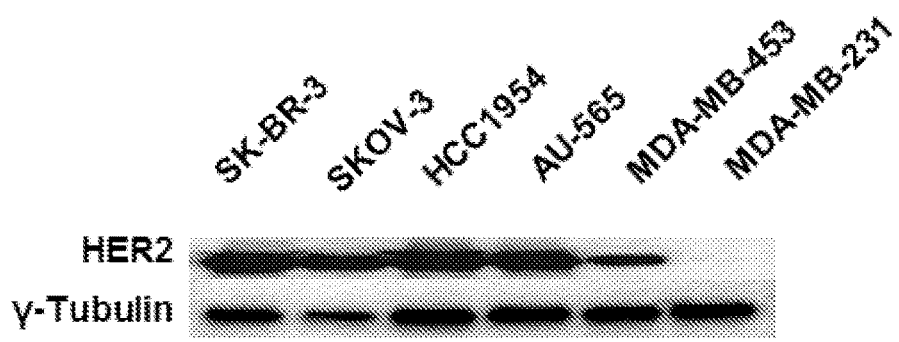
FIG. 1: A: Western blot of HER2 and γ-tubulin expression in SK-BR-3, SKOV-3, HCC1954, AU-565, MDA-MB-435 and MDA-MB-231 cells. B: Relative viability (MTT) of SK-BR-3, SKOV-3, AU-565, HCC1954 and MDA-MB-435 following 72 hrs treatment with indicated drugs. The sigmoidal curve fit model $a/(1+\exp(-(x-x_0)/b))$ was used for T-DM1. Data points represent the average of three independent experiments (trastuzumab, error bars: SE) or one representative of at least three separate experiments (T-DM1 and MH3-B1/rGel, error bars: SD).

To facilitate an understanding of the present invention, a number of terms and phrases are defined below:

As used herein, the term "antigen binding protein" refers to a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. Examples of antigen binding proteins include, but are not limited to polyclonal antibodies, monoclonal antibodies, chimeric antibodies, single chain antibodies, humanized antibodies, minibodies, Fab fragments, F(ab')2 fragments, Fv-fragments, single chain Fv-fragments, etc.

As used herein, the term "immunoconjugate" refers to a molecule comprising an antigen binding protein that is linked or joined to another agent such as a drug or toxin such as by a chemical linkage or a peptide linker. The term "immunoconjugate" encompasses antibody drug conjugates, immunotoxins and affinitytoxins. The antigen binding protein portion of the molecule may be an immunoglobulin or antigen binding fragment or antigen binding derivative thereof, for example polyclonal antibodies, monoclonal antibodies, chimeric antibodies, single chain antibodies, humanized antibodies, minibodies, Fab fragments, F(ab')2 fragments, Fv-fragments, single chain Fv-fragments, etc. The antigen binding protein portion may also be a protein ligand able to bind a cell surface antigen. For example, EGF may target EGF-receptors expressed on the cell surface.

As used herein, the term "antibody drug conjugate (ADC)" refers to a molecule comprising an antigen binding protein that is linked or otherwise joined, usually via a chemical linkage, to a drug molecule.

As used herein, the term "immunotoxin" refers to a molecule comprising an antigen binding protein that is linked or otherwise joined, usually via a peptide linker, to a toxin molecule.

As used herein, the term "affinitytoxin" refers to a molecule comprising a protein ligand able to bind a cell surface antigen, wherein the protein ligand is linked or otherwise joined, usually via a peptide linker, to a toxin molecule.

As used herein, cancer cells are "responsive" to an immunoconjugate when a measurable toxic response can be detected upon contact of the cells with the immunoconjugate.

As used herein, the terms "detect", "detecting", or "detection" may describe either the general act of discovering or discerning or the specific observation of a composition.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "amplification oligonucleotide" refers to an oligonucleotide that hybridizes to a target nucleic acid, or its complement, and participates in a nucleic acid amplification reaction. An example of an amplification oligonucleotide is a "primer" that hybridizes to a template nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. Amplification oligonucleotides may optionally include modified nucleotides or analogs, or additional nucleotides that participate in an amplification reaction but are not complementary to or contained in the target nucleic acid. Amplification oligonucleotides may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligonucleotide that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligonucleotide may provide a promoter sequence and serve as a template for polymerization (referred to as a "promoter-provider").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label. In some embodiments, the reporter molecule is an "exogenous reporter molecule."

The term "exogenous reporter molecule" refers to a reporter molecule or label that is not found in nature associated with a detection reagent (e.g., probe, nucleic acid, or antibody). Examples include, but are not limited to, enzymatic, fluorescent, radioactive, or luminescent reporter molecules.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer therapy, including but not limited to, therapies that utilize cancer biomarkers. In particular, the present invention relates to compositions and methods for the prediction of a subject's response to cancer therapies.

The increased focus on personalized medicine has together with our increasing knowledge on cancer biology revealed great potential for the use of biomarkers in cancer treatment. A spectrum of different biomarkers is already incorporated in clinical practice to predict patient survival, evaluate therapeutic efficacy or monitor disease progression. Predictive biomarkers enable careful selection of those patients most likely to benefit from a specific treatment, and hence, such knowledge is crucial in order to rationally exploit current and future high-cost targeted cancer therapeutics.

Accordingly, provided herein are systems and methods for determining, recommending, and/or administering a treatment to a subject with cancer (e.g., breast cancer) based on expression of a one or more of protein markers. The present invention is not limited to particular markers. In some embodiments, a combination of an antigen for an antibody (e.g., HER2, HER3, EGFR) and one or more additional markers (e.g., RAB5 (preferably RAB5A), RAB4, RAB11 and HSP90 or HER3 and EGFR) are detected alone or in combination. In some embodiments, expression levels of the combination or markers are combined to generate a compound expression index.

In some preferred embodiments, the present invention provides methods for treating cancer in a patient, comprising obtaining a sample comprising cancer cells from the patient; measuring the expression level of RAB5 in the cancer cells by an in vitro assay; and administering an effective amount of an immunoconjugate targeting a surface antigen of the cancer cells if the expression level of RAB5 in the cancer cell sample is increased as compared to a predetermined reference level; or administering an antigen binding protein that does not comprise a drug or toxin if the expression level of RAB5 in the cancer cell sample is decreased as compared to the predetermined reference level. The expression of any one of RAB5A, RAB5B or RAB5C or combinations thereof may be assayed. In some particularly preferred embodiments, the expression of RAB5A is assayed.

As described, in some preferred embodiments, the decision on whether to administer an immunoconjugate or an antigen binding protein that is not conjugated to a toxin or drug is based on comparison of the measured expression of RAB5, preferably RAB5A, in a patient sample as compared to a predetermined reference or threshold level. Those of skill in the art will recognize that the reference or threshold level may be determined by statistical procedures applied to expression data obtained from suitable patient populations. Suitable statistical methodologies are provided in the Examples, although those of skill in the art will recognize that other statistical procedures may also be utilized. It will further be recognized that different statistical procedures, or the same procedures run a different or expanded data set, may produce different reference or threshold levels. Accordingly, the present invention is not limited to the use of any particular reference or threshold level for the expression of any particular marker (e.g., RAB5A) or combination of markers. In this respect, in some embodiments, the methods of the present invention further comprise assaying the expression level of one or more of RAB4, RAB11 or HSP90. In some preferred embodiments, the expression levels in a sample of one or more of RAB4, RAB11 or HSP90 are incorporated into an expression index with the RAB5 expression level, preferably the RAB5A expression level, and administering the effective amount of an immunoconjugate targeting a surface antigen of the cancer cells if the expression index is increased as compared to predetermined reference level.

In some preferred embodiments, the patient sample used in the methods of the present invention comprises cancer cells. Suitable sample containing cells may be obtained by a variety of methods including, but not limited to, biopsies, samples from surgery and samples from blood draws. In some preferred embodiments, the samples have been previously assayed for the present of one or more cell surface antigens. In some embodiments, the methods further comprise assaying the sample for the expression of one or more cell surface antigens if the sample has not been previously characterized. The present invention is not limited to the assay of any particular cell surface antigen, however cell surface antigens prone to internalization (e.g. by endocytosis) are preferred. Exemplary cell surface antigens prone to internalization include, but are not limited to, HER2, HER3, EGFR, CD3ε, CD19, CD22, CD25, CD30, CD33, CD56, CEA (CD66e), CD74, CD79a, CD138, NaPi2b, gpNMB, TROP-2, GUCY2C, Nectin-4, SC-16, STEAP1, FRα, IL-2R, EpCAM, and MSLN.

In some particularly preferred embodiments, the samples contain breast cancer cells. In these embodiments, the breast cancer cells are preferably characterized for expression of Epidermal Growth Factor Receptor (HER1), HER2, and/or HER3. In even more preferred embodiments, the samples are assayed for, or have previously been assayed and identified as having, the HER2 receptor.

As discussed above, in some embodiments, a compound expression index is utilized in the methods of the present invention. The present invention is not limited to the use of any particular compound expression index. Examples of suitable compound expression indexes follow.

In some embodiments, the compound expression index is: relative HER2 expression×(1−(1−Relative RAB5 expression)×0.3)×(1−(1−Relative RAB4 expression)×0.6)×(1−(1−Relative HSP90 expression)×0.8)/(1−(1−(1/Relative RAB11 expression))×0.4).

In some embodiments, the compound expression index is: relative HER2 expression×(1−(1−Relative RAB4 expression)×0.6)×(1−(1−Relative RAB5 expression)×0.3)×(1−(1−Relative HSP90 expression)×0.8).

In some embodiments, the compound expression index is: relative HER2 expression×(1−(1−Relative RAB4 expression)×0.6)×(1−(1−Relative RAB5 expression)×0.2)×(1−(1−Relative HSP90 expression)×0.6).

In some embodiments, the compound expression index is: relative HER2 expression×(1−(1−Relative RAB4 expression)×0.4)×(1−(1−Relative RAB5 expression)×0.2).

In some embodiments, the compound expression index is: relative HER2 expression×(1−(1−Relative RAB5 expression)×0.3)×(1−(1−Relative RAB4 expression)×0.6).

In some embodiments, the compound expression index is: relative HER2 expression×(1−(1−Relative RAB5 expression)×0.3).

In some embodiments, the compound expression index is: relative HER2 expression×(1−(1−Relative RAB4 expression)×0.4).

In some embodiments, the compound expression index is: relative HER2 expression×(1−(1−Relative RAB4 expression)×0.6).

In some embodiments, the compound expression index is: relative HER2 expression×(1−(1−Relative RAB11 expression)×0.2).

In some embodiments, the compound expression index is: relative HER2 expression×(1−(1−Relative HSP90 expression).

In some embodiments, the expression is protein expression. In some embodiments, the determining step comprises an immunoassay. In some embodiments, the expression is mRNA expression. In some embodiments, the determining step comprises reverse transcription of the mRNA to provide cDNA and amplification of the cDNA with primers specific for the biomarker. In some embodiments, the detection technique is RT-PCR.

The expression assays utilized in the present invention may utilize a single biomarker such as RAB5A, or a panel of biomarkers (e.g., RAB5A and one or more of RAB4, RAB11 or HSP90; RAB5A and HER2; or RAB5A, HER2 and one or more of RAB4, RAB11 or HSP90). In some embodiments, the panels or assays of the present invention comprise less than 100, 75, 50, 25, 20, 15, 10, or five biomarkers, or, in other preferred embodiments, up to 1, 2, 3, 4, 5, 6, 7, 8, 9, 10 or 20 biomarkers in total.

In some embodiments, the levels of protein expression are detected in a sample from a subject. In some embodiments, the subject has been diagnosed with cancer (e.g., breast cancer). In some embodiments, the sample is tissue (e.g., biopsy tissue), blood, serum, urine, etc.

Exemplary methods of detecting protein markers are provided below. However, any suitable method of detecting tumor marker proteins may be utilized.

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldifluoride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

In some embodiments, immunomagnetic detection is utilized. In some embodiments, detection is automated. Exemplary immunomagnetic detection methods include, but are not limited to, those commercially available from Veridex (Raritan, NJ).

In some embodiments, a computer-based analysis program is used to translate the raw data generated by the detection assay (e.g., the presence, absence, or amount of marker expression) into data of predictive value for a clinician (e.g., choice of cancer therapy or compound expression index). The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a blood or serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of cancer treatment being successful or compound expression index) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

Compositions for use in the diagnostic, prognostic, and treatment methods of the present invention include, but are not limited to, probes, amplification oligonucleotides, and antibodies. Particularly preferred compositions detect the presence of level of expression of markers in a sample.

Any of these compositions, alone or in combination with other compositions of the present invention, may be provided in the form of a kit. For example, the single labeled probe and pair of amplification oligonucleotides or antibodies and immunoassay components may be provided in a kit for the amplification and detection of markers. Kits may further comprise appropriate controls and/or detection reagents.

The probe and antibody compositions of the present invention may also be provided in the form of an array or panel assay.

In some embodiments, the present invention provides systems, kits and methods for determining and administering a treatment course of action.

The methods of the present invention find use in the treatment of a variety of cancers. Cancers that may be treated according to the present invention include, but are not limited to, breast cancer, colorectal cancer, lung cancer, prostate cancer, melanoma, glioblastoma, pancreatic cancer, renal cell carcinoma, ovarian cancer, bladder cancer, endometrial cancer, gastrointestinal cancer, mesothelioma, multiple myeloma, acute myelogenous leukemia, acute lymphoblastic leukemia, and Non-Hodgkin's Lymphoma. As described above, in preferred embodiments where the expression level of a biomarker or combination of biomarkers is increased in a patient sample as compared to a reference or threshold expression level or compound expression index, then a call is made to administer an immunoconjugate to the patient. Likewise, in other preferred embodiments where the expression level of a biomarker or combination of biomarkers is decreased in a patient sample as compared a reference or threshold expression level or compound expression index, then a call is made to administer an antigen binding protein that is not conjugated to a drug or toxin to the patient. In embodiments where administration of an immunoconjugate is called for, then an immunoconjugate that binds to a surface antigen expressed by the tumor or cancer cells in the patient is selected. Suitable surface antigens to which the immunoconjugate may be directed to include, but are not limited to, HER2, HER3, EGFR, CD3ε, CD19, CD22, CD25, CD30, CD33, CD56, CEA (CD66e), CD74, CD79a, CD138, NaPi2b, gpNMB, TROP-2, GUCY2C, Nectin-4, SC-16, STEAP1, FRα, IL-2R, EpCAM, and MSLN.

In some embodiments, the immunoconjugate is an antibody drug conjugate. Suitable antibody drug conjugates include, but are not limited to, Trastuzumab emtansine (T-DM1, Kadcyla), Brentuximab vedotin (SGN-35), Inotuzumab ozogamicin (CMC-544), Pinatuzumab vedotin (RG-7593), Polatuzumab vedotin (RG-7596), Lifastuzumab vedotin (DNIB0600A, RG-7599), Glembatuzumab vedotin (CDX-011), Coltuximab ravtansine (SAR3419), Lorvotuzumab mertansine (IMGN-901), Indatuximab ravtansine (BT-062), Sacitizumab govitecan (IMMU-132), Labetuzumab govitecan (IMMU-130), Milatuzumab doxorubicin (IMMU-110), Indusatumab vedotin (MLN-0264), Vadastuximab talirine (SGN-CD33A), Denintuzumab mafodotin (SGN-CD19A), Enfortumab vedotin (ASG-22ME), Rovalpituzumab tesirine (SC16LD6.5), Vandortuzumab vedotin (DSTP3086S, RG7450), Mirvetuximab soravtansine (IMGN853), ABT-414, IMGN289, or AMG595. In some embodiments, the antibody toxin conjugate is MH3-B1/rGel, denileukin diftitox (DAB3891L2), moxetumomab pasudotox (CAT-8015), oportuzumab monotox (VB4-845), Resimmune, LMB-2, DT2219ARL, HuM195/rGel, RG7787, MOC31PE or D2C7-IT. As discussed above, the choice of which antibody drug conjugate to use in the methods of the present invention will depend on what specific surface antigens are expressed by the cancer cells in the subject.

In some embodiments, the immunoconjugate is an immunotoxin. Suitable immunotoxins include, but are not limited to, MH3-B1/rGel, denileukin diftitox (DAB389IL2), moxetumomab pasudotox (CAT-8015), oportuzumab monotox (VB4-845), Resimmune, LMB-2, DT2219ARL, HuM195/rGel, RG7787, MOC31PE or D2C7-IT. Again, as discussed above, the choice of which immunotoxin to use in the methods of the present invention will depend on what specific surface antigens are expressed by the cancer cells in the subject.

EXPERIMENTAL

The following examples are provided to demonstrate and further illustrate certain embodiments of the present invention and are not to be construed as limiting the scope thereof.

Example 1

Materials and Methods
Cells and Culturing.
Five HER2-expressing human cell lines were used in this study; the breast cancer cell lines SK-BR-3, AU-565 (CRL-2351), HCC1954 (CRL-2338) and MDA-MB-453 (HTB-131) and the ovarian cancer cell line SKOV-3 (HTB-77). The HER2 negative human breast cancer cell line MDA-MB-231 was used as a negative control for HER2 expression. All cell lines were obtained from American Type Culture Collection (Manassas, Va., USA), except SK-BR-3, kindly provided by the Department of Biochemistry, Institute for Cancer Research, Norwegian Radium Hospital, Oslo University Hospital, Oslo, Norway. All cell lines were used between passage number 3 and 25 to avoid changes in the cell line characteristics with time, and the cells were routinely checked for mycoplasma infections. SK-BR-3 and SKOV-3 cells were cultured in McCoy's 5A medium, AU-565, HCC1954 and MDA-MB-231 cells in RPMI-1640 medium (both obtained from Sigma-Aldrich, St. Louis, Mo., USA), while MDA-MB-453 were cultured in Leibovitz's L-15 medium (Lonza, Verviers, Belgium). All media were supplemented as previously described[19].

Cytotoxicity Experiments.
Cells were seeded at $8 \times 10^3$ (SK-BR-3), $1.8 \times 10^3$ (SKOV-3), $6 \times 10^3$ (AU-565), $4 \times 10^3$ (HCC1954) or $1 \times 10^4$ cells/well (MDA-MB-453) in 96-well plates (Nunc, Roskilde, Denmark) and allowed to attach overnight. The cells were then incubated with trastuzumab (Herceptin®, Roche, Basel, Switzerland), T-DM1 (ado-trastuzumab emtansine, Kadcyla®, Genentech, San Francisco, Calif., USA), MH3-B1/rGel or rGel (expressed and purified as previously described '[3]' at increasing concentrations for 72 hrs, after which cell viability was assessed by the MTT assay, as previously described[21]. $IC_{50}$ values were calculated from sigmoidal curves (fit model: $a/(1+\exp(-(x-x0)/b))$).

Western Blot Analysis.
Total cell extracts were obtained and analyzed by western blot as previously described[19]. Blot transfer of proteins was done using Trans-Blot® Turbo™ Transfer System (Bio-Rad Laboratories, CA, USA). Cellular protein expression was detected using EGFR (#4267), HER2 (#2165), HER3 (#12708), HSP90 (#4877) antibodies from Cell Signaling Technology (Danvers, Mass., USA), Rab5 (610281) and Rab11 (610656) antibodies from BD Biosciences (San Jose, Calif., USA) and a Rab4 (R5780) antibody from Sigma-Aldrich. Protein expression was correlated to γ-tubulin as detected by an antibody (#T6557) from Sigma-Aldrich. Supersignal West Dura Extended duration Substrate (Thermo Scientific, Rockford, Ill., USA) and ChemiDoc™ densitometer (Bio-Rad) was used for the detection of protein bands on the membrane. ImageLab 4.1 (Bio-Rad) (software) was used for quantification of protein expression. The expression of each protein was calculated relative to the highest expressing cell line.

Correlation Analysis.
The relative expression of HER2, HER3, EGFR, Rab4, Rab5, Rab11 and HSP90 in the cell lines was plotted against the cell line sensitivity towards the two HER2-targeted therapeutics, as measured by $1/IC_{50}$(T-DM1) or targeting index (TI) (MH3-B1/rGel), and a linear regression was assessed. Several proteins may impact on T-DM1 or MH3-B1/rGel toxicity together with HER2. The level of impact as compared to HER2 may, however, vary. It was here calculated if the $R^2$ values obtained by $1/IC_{50}$(T-DM1) or TI (MH3-B1/rGel) linearly correlated to HER2 could be increased by incorporating the relative expression of other proteins (HER3, EGFR, Rab4, Rab5, Rab11 and HSP90) into the regressions. These regression curves were established with decreasing contribution factors ranging from 1 to 0 for each protein together with HER2 using the formula:

HER2×(1−(1−Protein)×F) for curves with a positive slope and

HER2/(1−(1−Protein)×F) for curves with a negative slope where HER2 is the relative expression of HER2, Protein is the relative expression of the protein of interest and F is the contribution factor ranching from 1 to 0.

The $R^2$ values were plotted as a function of contribution factor for each protein. Proteins with belonging contribution factor resulting in an increase in $R^2$ compared to the one obtained with HER2 alone were incorporated in a final regression curve for the T-DM1 and MH3-B1/rGel sensitivity in order to set the combination of expression parameters with the highest correlation to T-DM1- and MH3-B1/rGel-sensitivity as measured by $R^2$.

Results

The Efficacy of T-DM1 and MH3-B1/rGel is not Correlated to Trastuzumab Sensitivity.

Figure 1B:
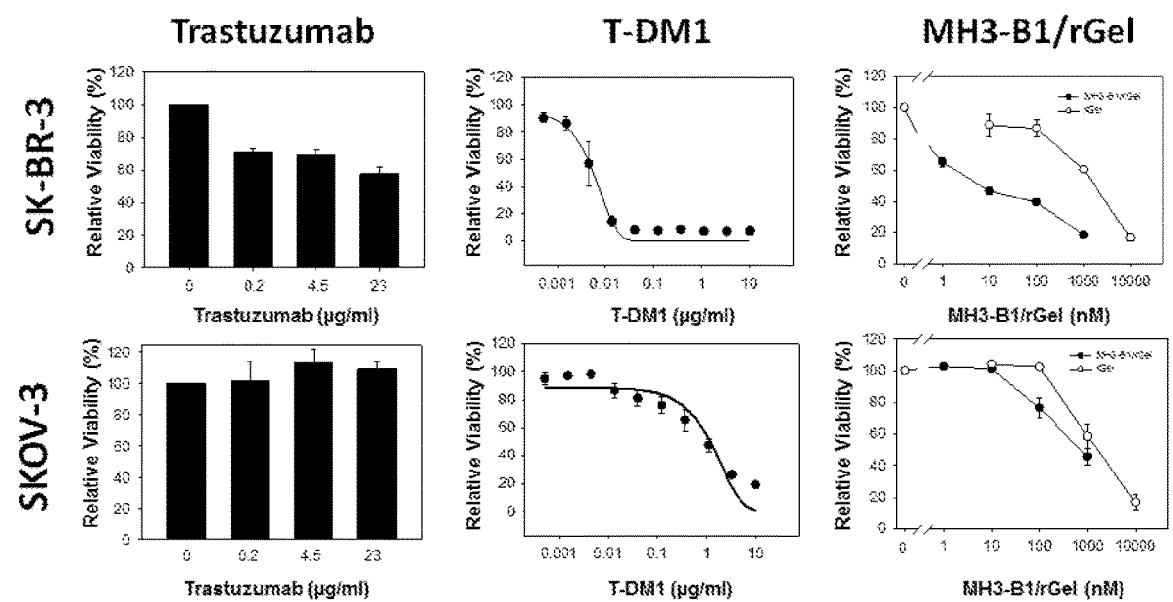
Figure 1B:
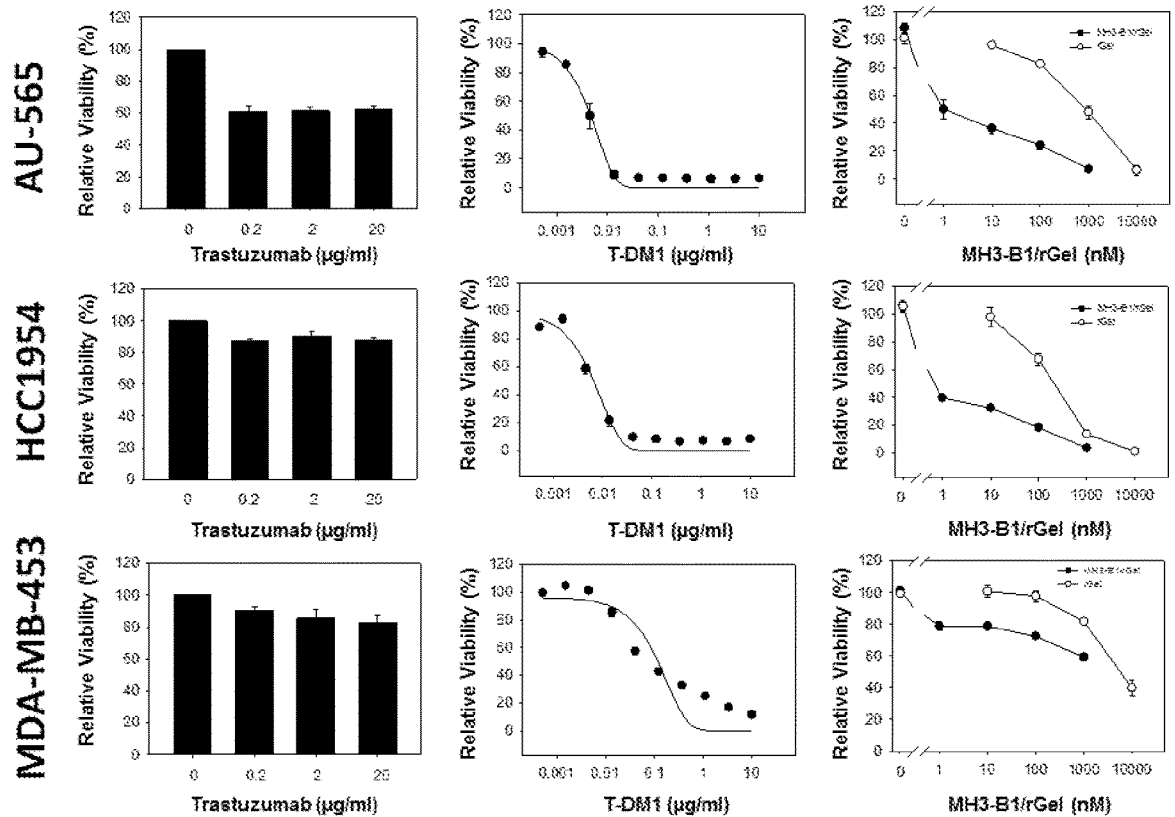

Strong HER2 expression was documented in the five HER2 expressing cell lines used in the present study compared to the low expression in MDA-MB-231 reported as HER2 negative (FIG. 1A)[22]. The antiproliferative effects of the HER2-targeted mAb trastuzumab and the intracellular acting HER2-targeted therapeutics T-DM1 and MH3-B1/rGel were established in the five HER2-positive cell lines (FIG. 1B). Subjecting the cells to a 72 hrs treatment with trastuzumab, T-DM1 or MH3-B1/rGel revealed the SK-BR-3 and AU-565 cells as highly sensitive to all three therapeutics, whereas the SKOV-3 cells, on the contrary, were found non-responsive to trastuzumab and exhibited low sensitivity to T-DM1 and MH3-B1/rGel as demonstrated by a relatively high $IC_{50}$ of 1.2 µg/ml and low $TI_{50}$ of 2.4, respectively (FIGS. 1 and 2B). The HCC1954 and MDA-MB-453 cells were both found low- to moderately sensitive to trastuzumab treatment, but responded different to the intracellular acting HER2-targeted therapeutics with the HCC1954 cells showing high sensitivity to both T-DM1 and MH3-B1/rGel, whereas the MDA-MB-453 cells showed low sensitivity to these two drugs (FIGS. 1 and 2B). No clear connection was therefore found between trastuzumab sensitivity and sensitivity towards T-DM1 and MH3-B1/rGel among the five cell lines (FIGS. 1 and 2B). Even though T-DM1 and MH3-B1/rGel have clearly distinct action points within the cell, a coherence was revealed between the sensitivity towards these two therapeutics among the cell lines where high/low response towards one of the two therapeutics seemed to predict a similar high/low response towards the other.

Figure 2A:
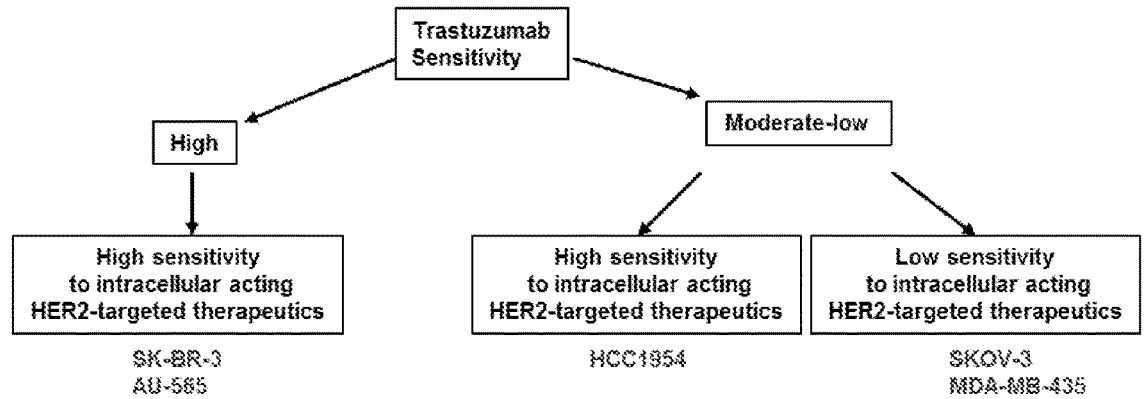
FIG. 2: A: Schematic presentation of the cellular sensitivity to trastuzumab and HER2-targeted intracellular acting therapeutics. B: Cellular sensitivity towards trastuzumab, T-DM1 and MH3-B1/rGel among SK-BR-3, SKOV-3, AU-565, HCC1954 and MDA-MB-435 cells. $IC_{50}$: drug concentration that inhibits viability of 50% of the cells. TI: $IC_{50}$(rGel)/$IC_{50}$(MH3-B1/rGel). Representative (C) and quantified (D) Western blots (n=2) of HER2 (D1), HER3 (D2), EGFR (D3) and γ-tubulin expression in SK-BR-3, SKOV-3, AU-565, HCC1954 and MDA-MB-435 cells. Linear regression analysis curves between HER2 and T-DM1 sensitivity (1/$IC_{50}$(T-DM1)) (E1) or MH3-B1/rGel sensitivity (TI) (E2).

Based on these findings, the cell lines were classified into three categories; (i) high sensitivity to trastuzumab, T-DM1 and MH3-B1/rGel (SK-BR-3 and AU-565), (ii) low/moderate sensitivity to trastuzumab, T-DM1 and MH3-B1/rGel (SKOV-3 and MDA-MB-453), (iii) low/moderate sensitivity to trastuzumab, but high sensitivity to T-DM1 and MH3-B1/rGel (HCC1954) (FIG. 2A).

The Correlation of HER2 Expression and T-DM1 Toxicity is Stronger than Observed for MH3-B1/rGel Toxicity.

HER2 expression is essential for both T-DM1 and MH3-B1/rGel toxicity. However, the level of expression may not necessarily correlate directly to drug sensitivity due to differences in drug processing (e.g. uptake, intracellular transport and interaction with intracellular drug targets) between the cells. Quantification of HER2 expression in the five cell lines indicated AU-565 to have the highest expression level of HER2, closely followed by HCC1954 (0.9) and SK-BR-3 (0.8) (FIGS. 2C and D1). A 50% lower HER2 expression was found in the SKOV-3 cells compared to AU-565, and MDA-MB-453 was indicated as the cell line with the lowest HER2 expression in the panel (0.4) (FIGS. 2C and D1). The level of HER2 expression reported here is in agreement with recent reports[22, 23]. Furthermore, a linear relationship was found between HER2 expression and T-DM1 and MH3-B1/rGel sensitivity among the cell lines, resulting in $R^2$ values of 0.926 for T-DM1 and 0.800 for MH3-B1/rGel (FIGS. 2E1 and E2).

HER3 May Serve as an Additional Biomarker to HER2 for T-DM1 Sensitivity.

Figure 3A:
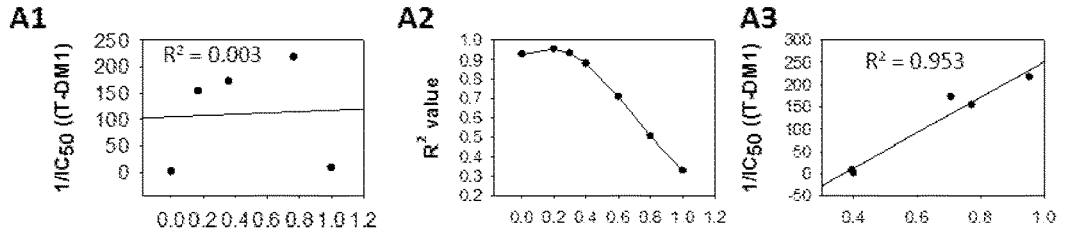
FIG. 3: Impact of HER3 and EGFR expression on T-DM1 (A and B) and MH3-B1/rGel (C, D and E) sensitivity together with HER2. A and B: The left panel shows linear regression analysis curves between HER3 (A1) or EGFR (B1) expression and T-DM1 sensitivity in the five cell lines. The middle panel illustrates $R^2$ values from the linear regressions as a function of the contribution factor from HER3 (A2) or EGFR (B2) expression in addition to that of HER2 expression on T-DM1 sensitivity in the five cell lines. A3 represents the optimized linear regression analysis curve where T-DM1 sensitivity is linearly correlated to both HER2 and HER3 expression (contribution factor: 0.2). B3 illustrates $R^2$ values from the linear regressions as a function of the factor of influence from EGFR expression in addition to that of HER2 expression and HER3 expression (contribution factor 0.2) on T-DM1 sensitivity in the five cell lines. C and D: The left panel shows linear regression analysis curves between HER3 (C1) or EGFR (D1) expression and MH3-B1/rGel sensitivity in the five cell lines. The middle panel illustrates $R^2$ values from the linear regressions as a function of the contribution from HER3 (C2) or EGFR (D2) expression in addition to that of HER2 expression on MH3-B1/rGel sensitivity in the five cell lines. The right panel represents optimized linear regression analysis curves where MH3-B1/rGel sensitivity is linearly correlated to both HER2 and HER3 expression (contribution factor: 0.4) (C3) or HER2 and EGFR expression (contribution factor: 0.3) (D3). E1 illustrates $R^2$ values from the linear regressions as a function of the factor of influence from HER3 expression in addition to that of HER2 and EGFR expression (contribution factor 0.3) on MH3-B1/rGel sensitivity in the five cell lines. E2 represents the optimized linear regression analysis curve where MH3-B1/rGel sensitivity is linearly correlated to HER2, EGFR (contribution factor 0.3) and HER3 expression (contribution factor: 0.4).
Figure 3B:
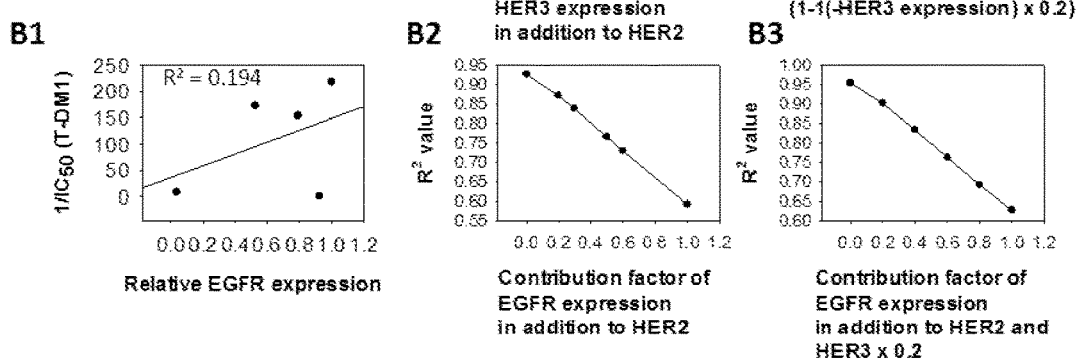
Figure 3C:
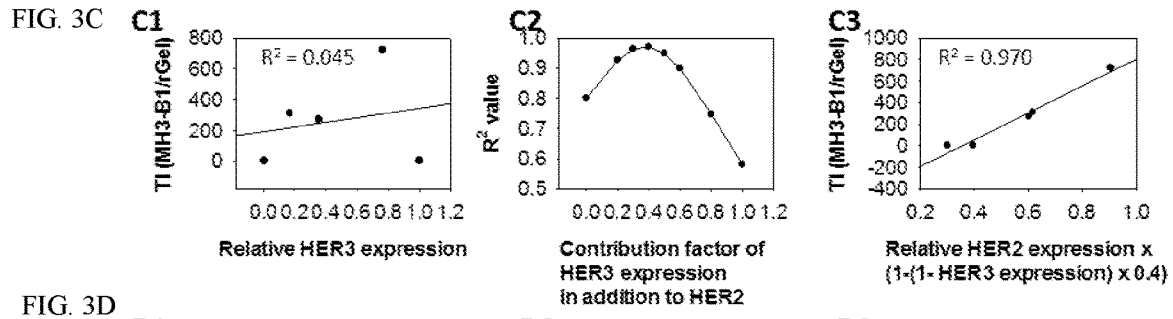
Figure 3D:
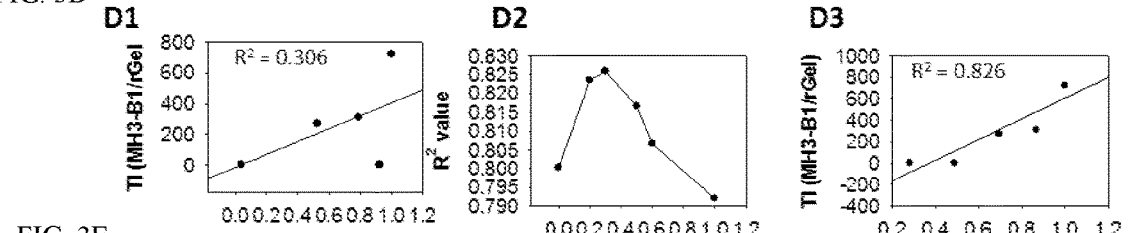
Figure 3E:
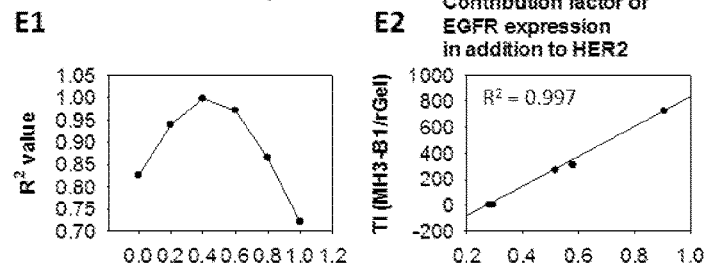

HER2 is known to complex with other members of the EGFR family. Hence, HER3 and EGFR were quantified to examine a relationship between T-DM1 and MH3-B1/rGel toxicity and expression of these two members of the EGFR family. The selected panel of cell lines was found to vary substantially in their level of both HER3 and EGFR expression (FIGS. 2C, 2D2 and 2D3). No clear correlation was, however, found between the level of HER3 or EGFR and the sensitivity towards T-DM1 (FIGS. 3A1 and B1) or MH3-B1/rGel (FIGS. 3C1 and D1). It was further evaluated if EGFR and HER3 could be correlated to T-DM1- and MH3-B1/rGel-sensitivity together with HER2. Establishing $R^2$ values for linear regressions of $1/IC_{50}$ (T-DM1) and HER2 together with HER3 with increasing contribution factors revealed a larger $R^2$ of 0.953 when HER3 expression was included in the correlation analysis with a contribution factor of 0.2 (FIGS. 3A2 and 3A3) compared to when HER2 was used alone ($R^2$=0.926, FIG. 2E1). No increase in linear correlation was detected by incorporating EGFR with increasing factors of influence into the regression analysis between T-DM1 sensitivity and HER2 expression (FIG. 3B2). Impact of EGFR expression in the regression between T-DM1 and HER2×HER3 (Contribution factor 0.2) was also evaluated. Also here, the $R^2$ values with increasing contribution factors of EGFR were all found less than observed with HER2 and HER3 (contribution factor 0.2) only (FIG. 3B3).

HER3 and EGFR May Serve as Additional Biomarkers to HER2 for MH3-B1/rGel Sensitivity.

Incorporating contribution of EGFR and HER3 into the regression analysis between MH3-B1/rGel sensitivity and HER2 expression resulted in increased $R^2$ values ($R^2$=0.970 for HER2×HER3 with contribution factor 0.4 and $R^2$=0.826 for HER2×EGFR with contribution factor 0.3) compared to those obtained by HER2 expression only (FIGS. 2E2, 3C2, 3C3, 3D2 and 3D3). Adding impact of HER3 expression with increasing contribution factors into the regression between HER2 and EGFR (contribution factor 0.3) and MH3-B1/rGel-sensitivity indicated an increased correlation as measured by increased $R^2$ values with the maximum observed with HER3 contribution factor 0.4 ($R^2$=0.997, FIGS. 3E1 and 3E2).

HER2-Expressing Cell Lines Differ in their Expression Level of Proteins Involved in Endocytic Trafficking.

As T-DM1 and MH3B1/rGel are dependent on internalization and intracellular trafficking in order to exert their intracellular mechanism of action, proteins involved in the endocytic machinery were quantified in the panel cell lines. These proteins included Rab5 (FIGS. 4A and B); implicated in the delivery of cargo from the plasma membrane to early endosomes as well as endosome fusion, Rab4; implicated in recycling from early endosomes (FIGS. 4A and C), HSP90 (FIGS. 4A and D) which is reported to regulate HER2 recycling and Rab11; involved in recycling through perinuclear recycling endosomes and plasma membrane-Golgi traffic (FIGS. 4A and E)[24,25]. The expression level of these proteins among the cell lines showed large differences and no simple connection was found between the expression levels.

Rab5 and Rab4 May Function as Additional Biomarkers to HER2 to Predict T-DM1 Sensitivity.

Figure 4A:
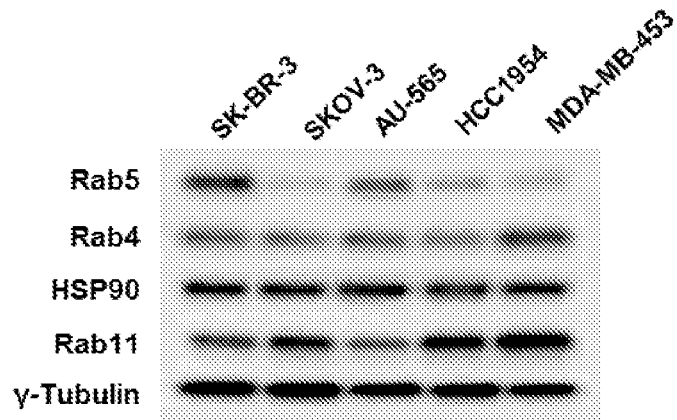
FIG. 4: Representative (A) and quantified (B-E) Western blots (n=2) of Rab5, Rab4, HSP90, Rab11 and γ-tubulin expression in SK-BR-3, SKOV-3, AU-565, HCC1954 and MDA-MB-435 cells.
Figure 4B:
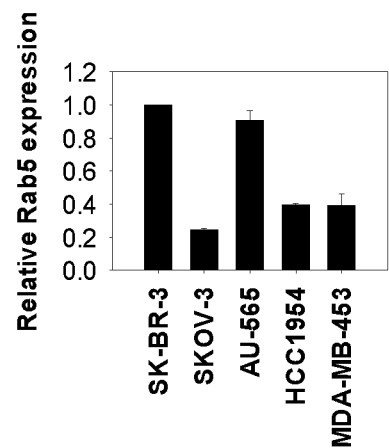
Figure 4C:
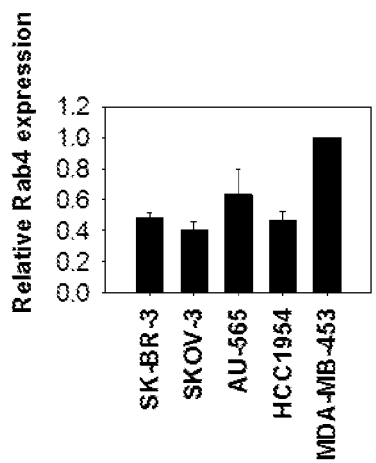
Figure 4D:
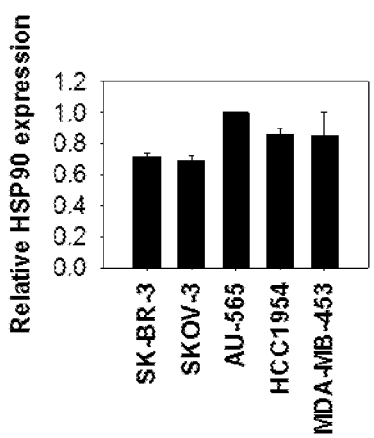
Figure 4E:
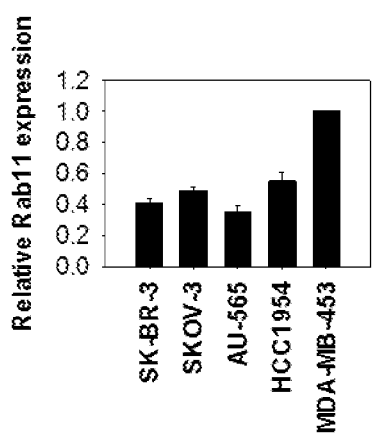

It was further assessed if the investigated proteins involved in the endocytic machinery (FIG. 4) had an impact on T-DM1 sensitivity among the cell lines. A 2.5-3 fold higher expression level of Rab5 was found in the highly T-DM1 sensitive SK-BR-3 and AU-565 cells compared to the other cell lines in the panel (FIGS. 4A and B). A relatively weak correlation was found between T-DM1 toxicity and Rab5 expression ($R^2$=0.643) (FIG. 5A1). Establishing linear regression curves for T-DM1 toxicity and HER2 expression with increasing contribution factors of Rab5 expression indicated Rab5 to impact on T-DM1 toxicity together with HER2 (FIG. 5A2). The maximal $R^2$ value for HER2 and Rab5 was found when Rab5 was added with a contribution factor of 0.3 (FIG. 5A2), increasing from 0.926 to 0.986 by including a 30% contribution from Rab5 (FIG. 5A3). No linear correlation was found between Rab4 expression and T-DM1 sensitivity (R2=0.088, FIG. 5B1). A minor increase in the $R^2$ value was found when the T-DM1 sensitivity was correlated to HER2 with a contribution factor of 0.4 from Rab4 (FIGS. 5B2 and 5B3). It was also investigated if Rab4 correlated inversely together with HER2 to T-DM1 sensitivity. No increased $R^2$ value compared to the one obtained with HER2 alone was, however, found when incorporating 1/Rab4 expression into the regression formula (data not shown). Linear regression of HSP90 expression and T-DM1 sensitivity also showed a poor correlation with a $R^2$ value of 0.266 (FIG. 5C1), and no increase in $R^2$ value compared to the one obtained with HER2 alone could be observed by incorporating influence of HSP90 into the regression formula with HER2 (FIG. 5C2). An inverse linear correlation ($R^2$=0.459) was found between Rab11 expression and T-DM1 sensitivity (FIG. 5D1). Linear regressions between T-DM1 sensitivity and HER2 with increasing contribution factors of 1/Rab11 expression showed almost no increase in $R^2$ value as compared to the one obtained with HER2 alone (0.929 versus 0.926, FIGS. 5D2 and 5D3).

Figure 5:
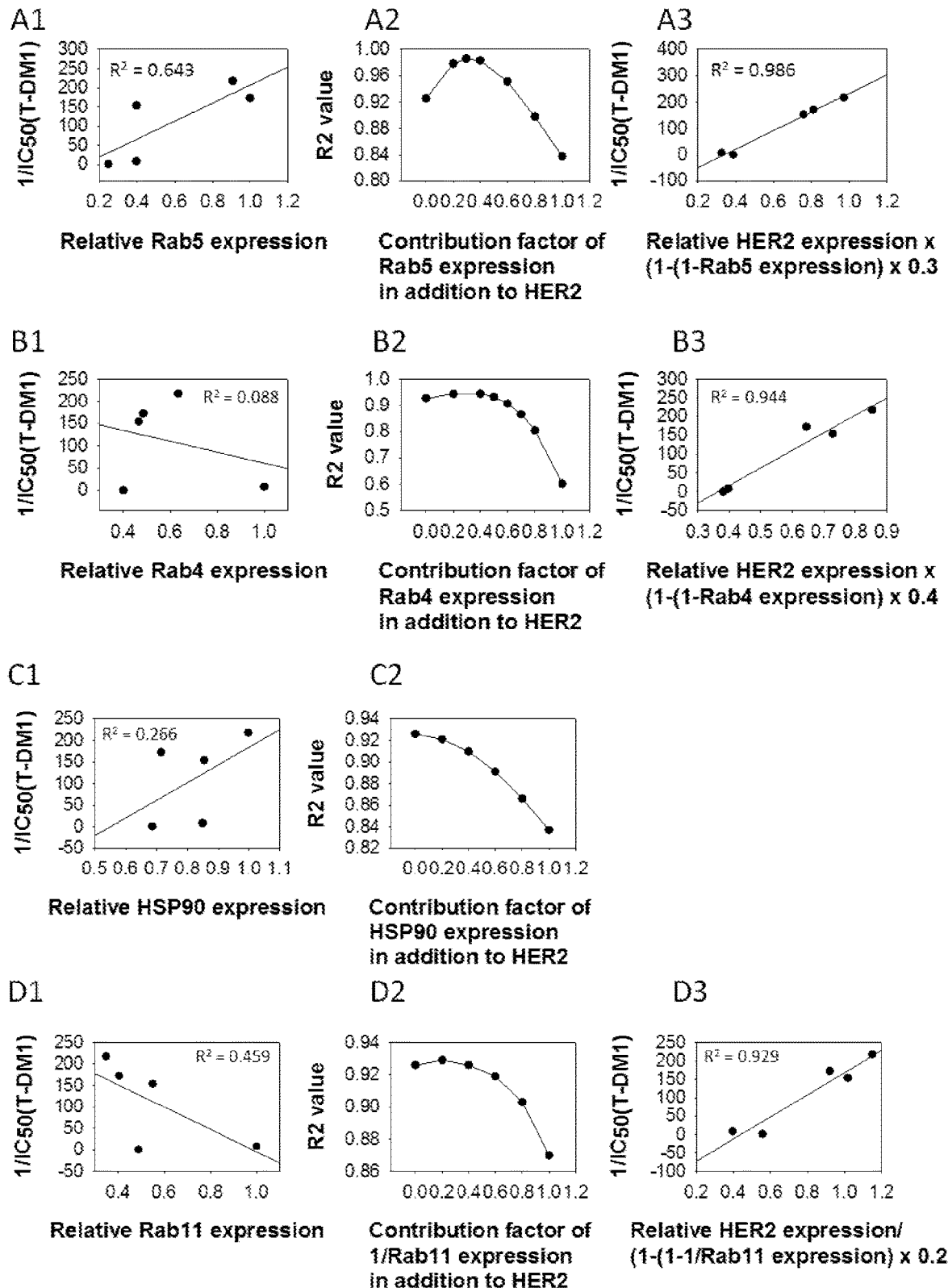
FIG. 5: Impact of Rab5, Rab4, HSP90 and Rab11 expression on T-DM1 sensitivity together with HER2. The left panel shows linear regression analysis curves between Rab5 (A1), Rab4 (B1), HSP90 (C1) or Rab11 (D1) expression and T-DM1 sensitivity in the five cell lines. The middle panel illustrates $R^2$ values from the linear regressions as a function of the factor of influence from Rab5 (A2), Rab4 (B2), HSP90 (C2) or 1/Rab11 (D2) expression in addition to that of HER2 expression on T-DM1 sensitivity in the five cell lines. The right panel represents optimized linear regression analysis curves where T-DM1 sensitivity is linearly correlated to both HER2 and Rab5 (contribution factor: 0.3) (A3), Rab4 (contribution factor: 0.4) (B3) or 1/Rab11 (contribution factor: 0.2) (D3) expression.

As illustrated in FIG. 5, the expression level of Rab5 and Rab4 were one by one indicated as possible biomarkers for T-DM1 sensitivity together with HER2. It was then evaluated if combining Rab5 and Rab4 together with HER2 further increased the correlation to T-DM1 sensitivity. No increase in $R^2$ value as compared to the one observed with HER2×0.3 Rab5 was, however, found when incorporating influence of Rab4 into the regression formulas (data not shown). Altogether, the best linear correlation to T-DM1 sensitivity was found with HER2 in combination with Rab5 only at an influence factor of 0.3 ($R^2$=0.986, FIG. 5A3).

Rab5, Rab4, HSP90 and Rab11 May all Function as Additional Biomarkers to HER2 for MH3-B1/rGel Sensitivity.

Figure 6:
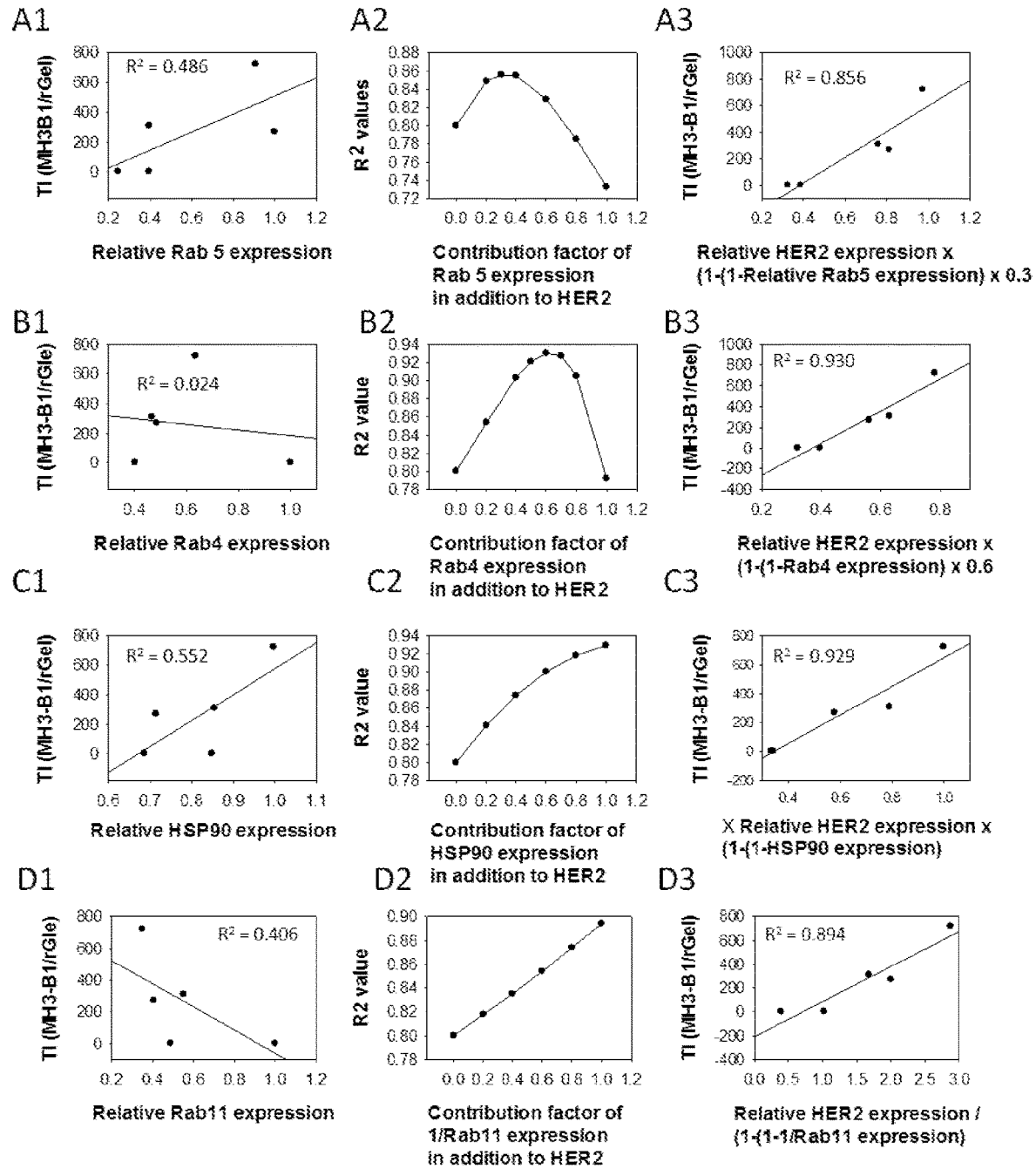
FIG. 6: Impact of Rab5, Rab4, HSP90 and Rab11 expression on MH3-B1/rGel sensitivity together with HER2. The left panel shows linear regression analysis curves between Rab5 (A1), Rab4 (B1), HSP90 (C1) or Rab11 (D1) expression and MH3-B1/rGel sensitivity in the five cell lines. The middle panel illustrates $R^2$ values from the linear regressions as a function of the factor of influence from Rab5 (A2), Rab4 (B2), HSP90 (C2) or 1/Rab11 (D2) expression in addition to that of HER2 expression on MH3-B1/rGel sensitivity in the five cell lines. The right panel represents optimized linear regression analysis curves where MH3-B1/rGel sensitivity is linearly correlated to both HER2 and Rab5 (contribution factor: 0.3) (A3), Rab4 (contribution factor: 0.6) (B3), HSP90 (contribution factor: 1) (C3) or 1/Rab11 (contribution factor: 1) (D3) expression.

The cellular expression level of Rab5, Rab4, HSP90 and Rab11 (FIG. 4) was also plotted against MH3-B1/rGel sensitivity, as measured by TI (FIG. 6). A linear correlation of Rab5 and TI was detected among the cell lines ($R^2$=0.486, FIG. 6A1). Incorporating Rab5 with increasing contribution factors into the established linear regression curves for HER2 and MH3-B1/rGel toxicity indicated Rab5 together with HER2 to impact on MH3-B1/rGel toxicity (FIG. 6A2), as visualized by increased $R^2$ values as compared to regression with HER2 only ($R^2$=0.800, FIG. 2E2). The highest $R^2$ value of 0.856 was found by including a 30% contribution from Rab5 (FIGS. 6A2 and 6A3), as also observed for the T-DM1 correlations (FIG. 5A3). No correlation was found between Rab4 expression and MH3B1/rGel sensitivity ($R^2$=0.024, FIG. 6B1). Utilizing Rab4 expression with increasing influence factors as an additional biomarker to HER2 strengthened, however, the linear correlation to TI as compared to HER2 only. The largest $R^2$ value of 0.930 was obtained by adding Rab4 with an influence factor of 0.6 to the HER2 and TI regression analysis (FIGS. 6B1 and 6B2). HSP90 and 1/Rab11 were also shown to correlate to MH3B1/rGel sensitivity, although not very strongly (R2=0.552 for HSP90 and 0.406 for 1/Rab11, FIGS. 6C1 and D1). HSP90 and 1/Rab11 was further shown one by one to increase the correlation of HER2 expression and MH3B1/rGel sensitivity with a maximum $R^2$ value obtained with the contribution factor of 1 for both proteins (FIGS. 6C2, C3, D2 and D3).

Figure 7:
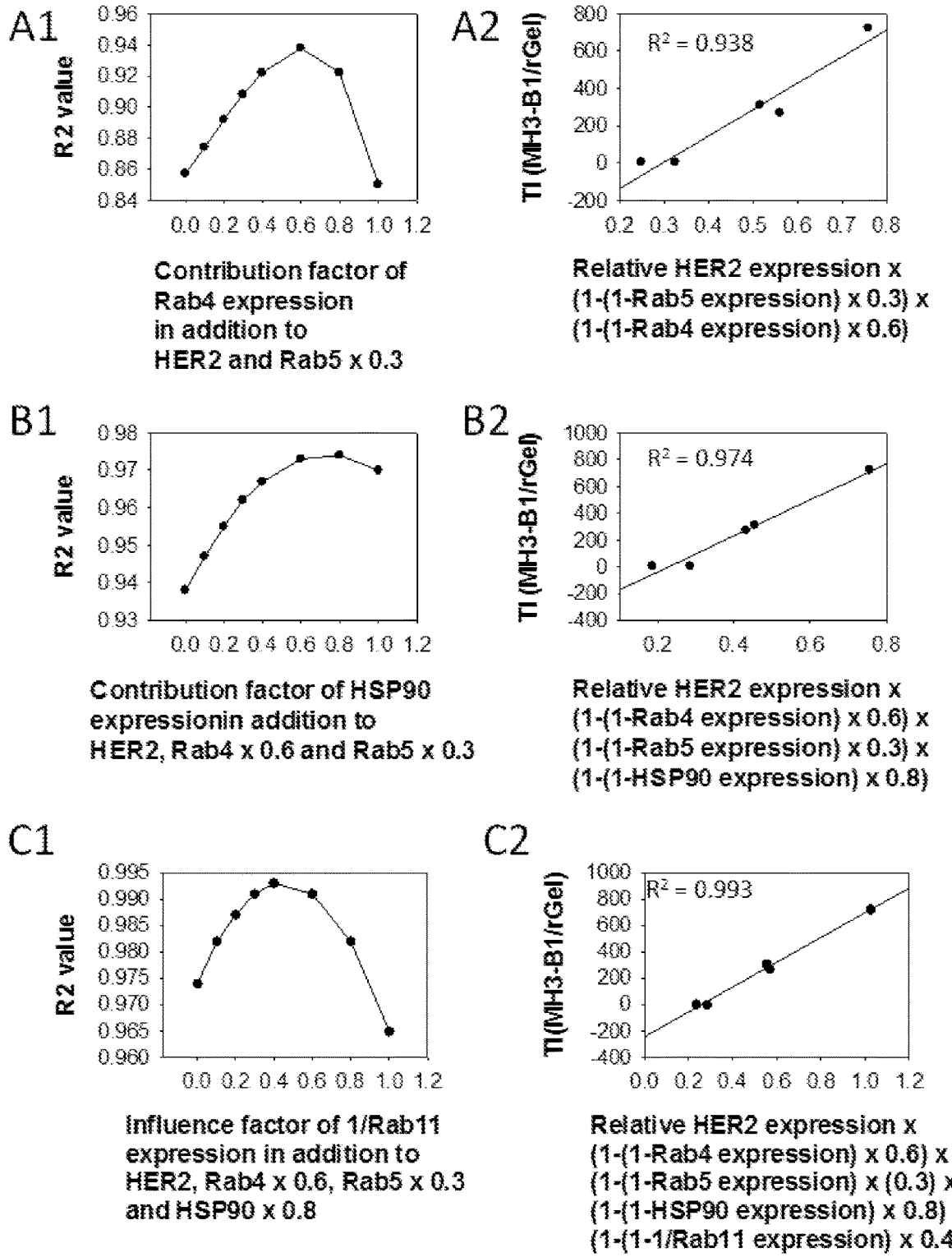
FIG. 7: Impact of a combination of Rab5, Rab4 and HSP90 or 1/Rab11 expression on MH3-B1/rGel sensitivity together with HER2. A1 illustrates $R^2$ values from the linear regressions as a function of the factor of influence from Rab4 expression in addition to that of HER2 and Rab5 expression (contribution factor 0.3) on MH3-B1/rGel sensitivity in the five cell lines. A2 represents the optimized linear regression analysis curve where MH3-B1/rGel sensitivity is linearly correlated to HER2, Rab5 (contribution factor 0.3) and Rab4 expression (contribution factor: 0.6). B1 illustrates $R^2$ values from the linear regressions as a function of the factor of influence from HSP90 expression in addition to that of HER2, Rab5 (contribution factor 0.3), and Rab4 (contribution factor 0.6) on MH3-B1/rGel sensitivity in the five cell lines. B2 represents the optimized linear regression analysis curve where MH3-B1/rGel sensitivity is linearly correlated to HER2, Rab5 (contribution factor 0.3), Rab4 expression (contribution factor 0.6) and HSP90 expression (contribution factor 0.8). C1 illustrates $R^2$ values from the linear regressions as a function of the factor of influence from 1/Rab11 expression in addition to that of HER2, Rab5 (contribution factor 0.3), Rab4 (contribution factor 0.6) and HSP90 (contribution factor 0.8) on MH3-B1/rGel sensitivity in the five cell lines. C2 represents the optimized linear regression analysis curve where MH3-B1/rGel sensitivity is linearly correlated to HER2, Rab5 (contribution factor 0.3), Rab4 expression (contribution factor 0.6), HSP90 expression (contribution factor 0.8) and 1/Rab11 expression (contribution factor 0.4).

As illustrated in FIG. 6 Rab5, Rab4, HSP90 and 1/Rab11 were all indicated as possible biomarkers one by one together with HER2 for MH3B1/rGel sensitivity. It was further studied if a combination of these 4 biomarkers together with HER2 would increase the correlation to MH3B1/rGel sensitivity further. The order of combining the different proteins into the regression formula was based on the route of endocytosis and trafficking starting with Rab5 (endocytosis) and then adding Rab4 (early recycling), HSP90 (early recycling) and 1/Rab11 (later recycling). As illustrated in FIG. 6A3, Rab5 (influence factor 0.3) together with HER2 correlated well with MH3B1/rGel sensitivity ($R^2$=0.856). Adding Rab4 expression with increasing factor of influence into the regression analysis increased, however, the $R^2$ value. The maximum $R^2$ value of 0.938 was reached when Rab4 was added with a contribution factor of 0.6 to that of HER2 and 0.3×Rab5 (FIGS. 7A1 and A2). HSP90 expression was further incorporated into the regression analysis with HER2, Rab5 and Rab4. A maximum $R^2$ value of 0.974 was obtained by including an 80% contribution from HSP90 into the regression analysis between MH3B1/rGel sensitivity and HER2, Rab5 (contribution factor 0.3) and Rab4 (contribution factor 0.6) (FIG. 7B). As illustrated in FIG. 6D, 1/Rab11 was shown to correlate well with MH3B1/rGel sensitivity together with HER2 ($R^2$=0.894). Adding impact of 1/Rab11 expression into the regression analysis between MH3B1/rGel sensitivity and HER2, Rab5, Rab4 and HSP90 expression also increased the $R^2$ value as shown in FIG. 7C1. The best correlation of 1/Rab11 expression together with the other proteins and MH3B1/rGel sensitivity was found with a factor of influence of 0.4 (FIG. 7C2), resulting in a maximum $R^2$ value of 0.993 when MH3B1/rGel sensitivity was correlated to HER2, Rab5 (contribution factor 0.3), Rab4 (contribution factor 0.6) and HSP90 (contribution factor 0.8) (FIG. 7C2). The regression analyses were also performed by adding contribution of the different proteins in a non-biological order without any major influence on the $R^2$ values obtained when correlated to MH3B1/rGel sensitivity (data not shown). Overall, the best correlation between MH3-B1/rGel toxicity and protein expression levels, established when adding contribution of the different proteins in a biological logic order, ($R^2$=0.993) (FIG. 7C2) was found when the TI was plotted against:

Relative HER2 expression×(1−(1−Relative Rab5 expression)×0.3)×(1−(1−Relative Rab4 expression)×0.6)×(1−(1−Relative HSP90 expression)× 0.8)/(1−(1−(1/Relative Rab11 expression))×0.4)

The field of biomarker-driven personalized cancer therapy has been rapidly growing along with an increasing number of clinically approved targeted anticancer therapeutics. Overall, the efficacy of drug-based personalized cancer therapy is dependent on the reliability of selected biomarkers to predict prognosis, response and/or resistance. The development of the HER2-targeted mAb trastuzumab represents a story of success in the field of biomarker-driven personalized cancer therapy as breast cancer patients classified as HER2 positive (~20% of all breast cancers) routinely receive trastuzumab as part of their treatment[26]. Another example is the assessment of BCR-ABL fusion in chronic myeloid leukemia (CML) for the use of imatinib, or EGFR and RAS wild type expression for the use of cetuximab in the treatment of colorectal cancer[27].

Most of the targeting drugs currently approved for the treatment of cancer are mAbs or small-molecular inhibitors for which the drug target also represents the target for mechanism of action. The target itself represents a clear biomarker for treatment with these drugs, even though additional biomarkers may be needed in order to deselect patients likely to experience resistance or low tolerability. Drug development in cancer therapy is, however, currently moving to more complex targeting therapeutics consisting of both a targeting moiety and a cytotoxic component such as a cytostatic drug (ADC) or a toxin (targeted toxin). For these multifunctional therapeutics other biomarkers associated with the intracellular transport and/or cytotoxic mechanism of action are likely to impact on the therapeutic outcome[15]. This is here indicated by the lack of coherence between trastuzumab and T-DM1/MH3-B1/rGel sensitivity in the selected panel of HER2 positive cell lines.

A strong linear correlation is here reported between cellular HER2 expression and response towards T-DM1 (FIG. 2E1). This is in agreement with several clinical studies demonstrating higher response rates of T-DM1 in patients with HER2 mRNA levels above the median compared to the below median subgroup[16, 17, 28]. The correlation between drug activity and HER2 expression is here indicated stronger for T-DM1 compared to MH3-B1/rGel (FIG. 2E2) as measured by the $R^2$ values, and this may be caused by differences in the cytotoxic components of these drugs. The cytotoxic component of T-DM1, (DM1), is a relatively small and lipophilic drug which, upon release from the trastuzumab component in the endocytic vesicle, is able to diffuse across the endocytic membrane and into the cytosol where it exerts its effect on the microtubule. This is in high contrast to the cytotoxic moiety of MH3-B1/rGel which is a 28 kDa hydrophilic type I ribosome-inactivating protein toxin (gelonin) that lacks an effective transport mechanism to enter the cytosol, but to some extent manage to enter the cytosol by a still unknown mechanism. The higher $R^2$ value obtained by correlation analysis of T-DM1 and HER2 expression compared to that of MH3-B1/rGel and HER2 expression probably reflects the differences in mechanisms for endocytic escape between these two drugs, where more obstacles are indicated for the gelonin pathway. A more complex route of intracellular release of gelonin, as compared to DM1, is also reflected in the magnitude of investigated proteins with impact on MH3-B1/rGel sensitivity (Rab5, Rab4, HSP90 and Rab11) as compared to Rab5 and Rab4 for T-DM1.

The cellular sensitivity to both T-DM1 and MH3-B1/rGel was here shown to correlate with HER3 in addition to HER2. The therapeutic effect of T-DM1 in a clinical phase III trial has previously been reported similar in HER3 expressing subgroups[17]. This is in agreement with the data shown here where no correlation is found between HER3 expression only and T-DM1 sensitivity (FIG. 3A1). However, the present report focuses on a mathematical approach in order to combine biomarkers with different contribution factors. These calculations indicate that HER3 in combination with HER2 may serve as a better biomarker for T-DM1 response compared to HER2 alone. HER3 is recognized as the preferred dimerization partner for HER2, and the heterodimer is reported to induce highly active tyrosine kinase signaling[19]. The correlation between T-DM1 and MH3-B1/rGel sensitivity and HER3 expression together with HER2 may therefore reflect an indirect inhibition of these heterodimers upon binding of trastuzumab and MH3-B1 to HER2. Compared to the full length antibody Trastuzumab in T-DM1, MH3-B1/rGel consist of a single chain fv fragment. Hence, binding of MH3-B1 to HER2 as part of heterodimers cannot be ruled out (both HER2/HER3 and HER2/EGFR). This is further indicated by the apparently stronger correlation between MH-3B1/rGel sensitivity ($R^2$ increased from 0.800 to 0.970) and HER3 expression in addition to HER2 (FIG. 8B1) as compared to T-DM1 ($R^2$ increased from 0.926 to 0.953, FIG. 8A1), as well as a minor increase in the $R^2$ value when the MH3-B1/rGel sensitivity was correlated to EGFR in addition to HER2 and HER3, while no such correlation was found for T-DM1 (FIGS. 8A1 and B1).

Rab5 is localized to early endosomes and regulate both endocytosis and endosome fusion of clathrin-coated vesicles[18]. Both T-DM1 and MH3-B1/rGel sensitivity was here shown to depend on Rab5 with a contribution factor of 0.3 in addition to HER2 (FIGS. 5A3 and 6A3). The similar impact of Rab5 on both HER2-targeting therapeutics together with HER2 (FIGS. 8A2 and B2) is probably related to the early function of Rab5 in endocytosis and subsequent endocytic trafficking, where the two drugs are likely to follow the same HER2-mediated pathway for endocytosis. Rab4 also acts early in the endocytic pathway by controlling recycling from early endosomes[30] and was here shown to correlate with the T-DM1 and MH3-B1/rGel sensitivity together with HER2 (FIGS. 5B3 and 6B3). A rapid recycling of HER2 may increase the cellular drug uptake, but also passively localize the drugs in early endosomes within the cell.

The increase in $R^2$ from 0.830 to 0.930 when incorporating Rab4 together with HER2 (FIG. 8B2) indicate cytosolic translocation from early endosomes as the mechanism for cytosolic release for MH3-B1/rGel. The minor contribution of Rab4 in addition to HER2 on T-DM1 sensitivity ($R^2$ increase from 0.926 to 0.944, FIG. 8A2) indicates that also emtansine to some extent is released from early endosomes, indicating that cytotolic translocation of emtansine does not solely rely on lysosomal sequestration of the trastuzumab moiety of T-DM1 as suggested in previous reports[7, 10]. It has previously been shown that Rab5 expression predict poor outcome in breast cancer patients and that Rab5/Rab4 recycling promotes extracellular matrix invasion and metastasis[31]. The present results may therefore indicate Rab5/Rab4 and HER2 positive breast cancer patients as promising candidates for T-DM1 and MH3-B1/rGel based therapy.

HSP90 is a HER2 chaperone and has been argued to inhibit HER2 degradation by several mechanisms including rapid recycling[32,33] HSP90 is here shown to correlate with MH3-B1/rGel toxicity together with HER2 (FIG. 8B2), in contrast to T-DM1 were no such correlation was found (FIG. 8A2). As commented for differences in Rab4 dependency, the difference in HSP90 impact on cytotoxicity of these drugs may reflect differences in mechanisms for cytosolic translocation. The difference may also be a result of the different HER2-targeting moieties between these drugs. Rab11 is, on the other hand, localized to the endocytic recycle compartment (ERC) and acts later in the endocytic process by recycling cargo back to the plasma membrane[34]. A negative correlation was here found between MH3-B1/rGel efficacy and Rab11 expression (FIG. 6B) indicating recycling and subsequent exocytosis to inhibit MH3-B1/rGel-efficacy. The lack of impact of Rab11 together with HER2 on T-DM1 toxicity (FIG. 5D) probably indicates T-DM1 and MH3-B1/rGel to follow distinct intracellular pathways in line with the chemical properties of their cytotoxic moieties. DM1 may e.g. plausibly escape the endocytic vesicles prior to accumulation in Rab11-positive recycling endosomes.

Figure 8:
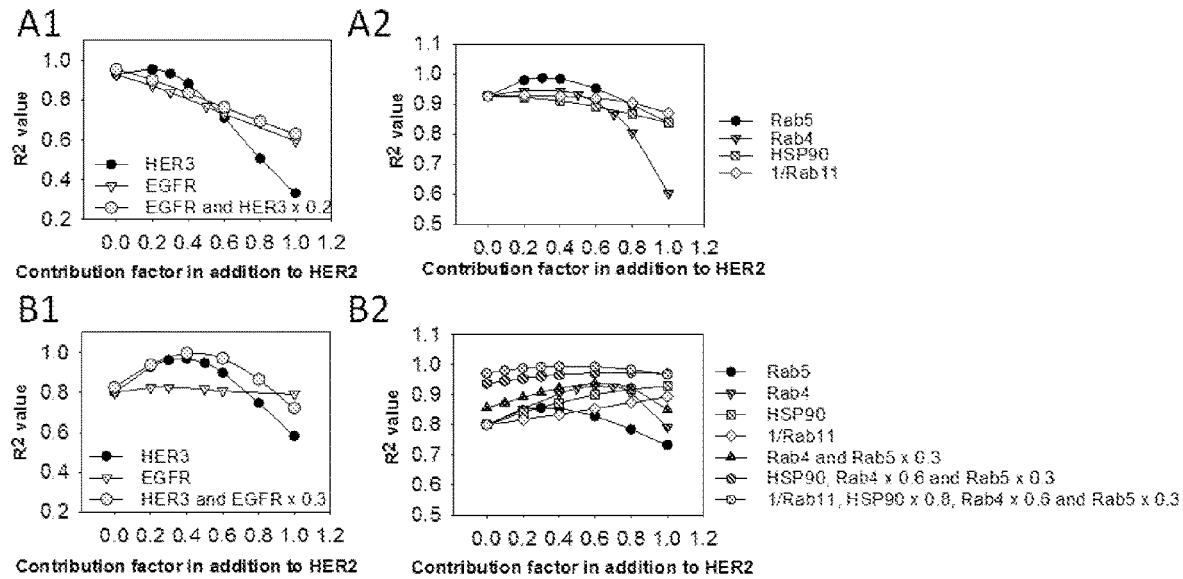
FIG. 8: Impact of a combination of HER3 and EGFR (A1, B1) or Rab5, Rab4, HSP90 and 1/Rab11 expression (A2, B2) together with HER2 on T-DM1 (A) or MH3-B1/rGel sensitivity (B). The presented results are the same as reported in FIGS. 5, 6 and 7, but here incorporated in the same figures. Schematic presentation of the indicated biomarkers for T-DM1 and MH3-B1/rGel sensitivity in the present report (C). Arrows indicate the drugs of which the current biomarker is suggested and the width of the arrows illustrates the protein impact on drug sensitivity. The circles indicate the two pools of biomarkers suggested for combination.
Figure 8C:
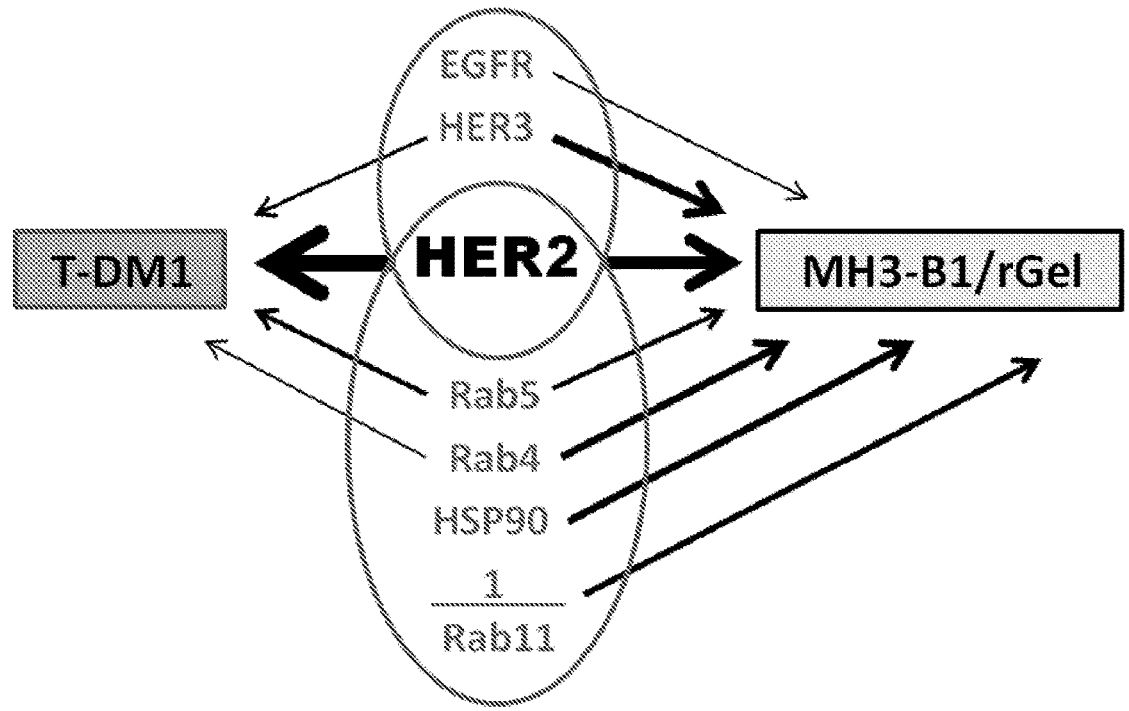

In total, six proteins were here tested as potential biomarkers together with HER2 for MH3-B1/rGel and T-DM1 response. The tested biomarkers were here divided in two groups reflecting either the targeting moiety of the HER2 targeting drugs (EGFR and HER3) or the intracellular transport component of the drugs (Rab5, Rab4, HSP90 and Rab11) (FIG. 8). The best correlation to drug sensitivity was obtained by pooling the biomarkers within these groups, and no increased correlation to drug sensitivity was shown by combining these two groups of biomarkers (data not shown). These results indicate the proteins in the two groups not to be fully independent, which is not surprising as endocytic trafficking of a drug clearly is dependent on cell binding and endocytosis. Hence, HER2 as a biomarker should be combined with either HER3 and EGFR or Rab4, Rab5, HSP90 and 1/Rab11 in order to predict cellular sensitivity towards T-DM1 and MH3-B1/rGel (FIG. 8). FIGS. 3, 5, 6 and 7 illustrate the impact of adding the six proteins as biomarkers with increasing contribution factors to that of HER2. The importance of the different proteins may, however, be compared as illustrated in FIGS. 8A and 8B were the R2 correlation data for both groups of biomarkers are incorporated in the same figures. An increased correlation to drug sensitivity was found for both HER2-targeting drugs by adding expression of the extracellular protein HER3 or the intracellular proteins Rab5 and Rab4 to that of HER2 as biomarkers, but with different impact on the $R^2$ value as visualized in FIGS. 8A, B and C. MH3-B1/rGel sensitivity was also to some extent shown dependent on EGFR expression in addition to HER2 and HER3, and on HSP90 and 1/Rab11 expression in addition to HER2, Rab5 and Rab4. The more complex pool of biomarkers correlating to MH3-B1/rGel sensitivity compared to T-DM1 may be caused by the more obstacled route of cytosolic translocation for MH3-B1/rGel compared to T-DM1 and may also reflect the difference in HER2-targeting moieties between these drugs.

In conclusion, the present report, for the first time, indicates that proteins involved in endocytic trafficking may be used, in addition to HER2, to predict the response to HER2-targeting therapeutics with intracellular action points. The impact of the different proteins seems, however, related to both the HER2-targeting moiety and the intracellular acting component of the drug, as well as the subsequent endocytic trafficking and mechanisms of cytosolic release. The future development of ADCs as well as other targeting drugs with intracellular mechanisms of action should incorporate a drug-dependent pool of biomarkers and include markers for uptake and cellular transport in addition to those of targeting and resistance mostly used today. A mathematical approach, as used here, could be used in order to establish pools of biomarkers with different factors of contribution to be used prognostic as well as therapeutic.

The general inventive concept described here is applicable to all antibody drug conjugates (ADCs) and antibody toxin conjugates (immunotoxins). Some preferred drugs which may be administered according to this method are presented in table 1 (ADCs) and table 2 (immunotoxins).

TABLE 1

Leading clinical stage ADCs

| Drug name | Target | Payload | Company |
| --- | --- | --- | --- |
| Brentuximab vedotin (SGN-35) | CD30 | MMAE | Seattle Genetics/Takeda |
| Trastuzumab emtansine (T-DM1) | HER2 | DM1 | Genentech (Roche) |
| Inotuzumab ozogamicin (CMC-544) | CD22 | Calicheamicin | Pfizer |
| Pinatuzumab vedotin (RG-7593) | CD22 | MMAE | Genentech (Roche) |
| Polatuzumab vedotin (RG-7596) | CD79a | MMAE | Genentech (Roche) |
| Lifastuzumab vedotin (DNIB0600A, RG-7599) | NaPi2b | MMAE | Genentech (Roche) |
| Glembatuzunnab vedotin (CDX-011) | gpNMB | MMAE | Celldex Therapeutics |
| Coltuximab ravtansine (SAR3419) | CD19 | DM4 | Sanofi Pasteur |
| Lorvotuzumab mertansine (IMGN-901) | CD56 | DM1 | Immunogen |
| Indatuximab ravtansine (BT-062) | CD138 | DM4 | Biotest |
| Sacitizumab govitican (IMMU-132) | TROP-2 | SN-38 | Immunomedics |
| Labetuzumab govitican (IMMU-130) | CEA (CD66e) | SN-38 | Immunomedics |
| Milatuzumab doxorubicin (IMMU-110) | CD74 | Doxorubicin | Immunomedics |
| Indusatumab vedotin (MLN-0264) | GUCY2C | MMAE | Takeda-Millenium |
| Vadastuximab talirine (SGN-CD33A) | CD33 | PBD dimer | Seattle Genetics |
| Denintuzumab mafodotin (SGN-CD19A) | CD19 | MMAF | Seattle Genetics |
| Enfortumab vedotin (ASG-22ME) | Nectin-4 | MMAE | Seattle Genetics/Astellas |
| Rovalpituzumab tesirine (SC16LD6.5) | SC-16 | D6.5 | Stemcentrx |
| Vandortuzumab vedotin (DSTP3086S, RG7450) | STEAP1 | MMAE | Genentech (Roche) |
| Mirvetuximab soravtansine (IMGN853) | FRα | DM4 | Immunogen |
| ABT-414 | EGFR | MMAF | AbbVie |
| IMGN289 | EGFR | DM1 | Immunogen |
| AMG595 | HER3 | DM1 | Amgen |

TABLE 2

| Leading clinical stage immunotoxins | | | |
|---|---|---|---|
| Drug name | Target | Payload | Company |
| Denileukin diftitox (DAB389IL2) | IL-2R | DT | Eisai Medical Research |
| Moxetumomab pasudotox (CAT-8015) | CD22 | PE | MedImmune |
| Oportuzumab monatox (VB4-845) | EpCAM | PE | Viventia |
| Resimmune | CD3e | DT | AngImmune |
| LMB-2 | CD25 | PE | Academic (US) |
| DT2219ARL | CD19/CD22 | DT | Academic (US) |
| HuM195/rGel | CD33 | Gelonin | Academic (US) |
| RG7787 | MSLN | PE | Genentech/Roche |
| MOC31PE | EpCAM | PE | Academic (NO) |
| D2C7-IT | EGFR | PE | Academic (US) |

Example 2

Patient Population.

Pre-treatment expression and pathologic complete response (pCR) data were available for 52 patients in a T-DM1+Pertuzumab (TDM1+P) group and 31 patients from the trastuzumab control (TH) group were available for analysis. Patients who progressed, withdrew consent, left the treating institution, or received non-protocol therapy prior to surgery are considered non-pCR for this analysis. The Table below shows the pCR rates by HR subtype within each arm:

|  | HR−HER2+ | HR+HER2+ |
|---|---|---|
| TDM1 + P | 12/17 | 18/35 |
| TH | 5/12 | 3/19 |

Expression Data.

All I-SPY 2 samples are analyzed on one of two Agilent custom arrays (the 15746 and 32627 designs). All samples in the TDM1+P arm was assayed on the 32627 arrays, while the TH arm was split between the platforms, with 22 samples on the older 15746 platform and 9 samples on the 32627 array. To combine data across the two designs, we have updated the probe annotation of the 15746 platform (September 2016); and for each platform, collapsed the normalized expression data by averaging such that genes represented by multiple probes are computed as the average across probes. The ComBat algorithm was then applied to adjust for platform-biases and combine the data from the two platforms. This procedure was performed for the pre-treatment data of the first 880 I-SPY 2 patients irrespective of experimental arm. The combined, platform-adjusted data from the TH and TDM1+P arms along with the annotation files for the 32627 and updated 15746 array designs are included in this delivery.

Qualifying Biomarker Analysis.

Normalized, platform-corrected pre-treatment expression levels of RAB5A, RAB4A, RAB11A, and HSP90AA1 were first tested individually as specific biomarkers of response to TDM1+P as per the qualifying biomarker evaluation (QBE) plan.

Step 1: Evaluate Biomarkers as Specific Predictor of Response to TDM1+P
Model 1A: pCR~Biomarker in TDM1+P Arm
Model 1B: pCR~Biomarker in TH Arm
Model 1C: pCR~Treatment+Biomarker+Treatment×Biomarker
Model 1D: pCR~Treatment+Biomarker+Treatment×Biomarker+HR status Of the biomarkers evaluated, only RAB5A is associated with response in the TDM1+P arm (likelihood ratio (LR) test p=0.012), but not the control arm (LR test p=0.242). The p value for the interaction between RAB5A expression and treatment is 0.024, which remains <0.05 after adjusting for HR status. Table below summaries results for the four biomarkers evaluated.

RAB5A succeeded as a continuous qualifying biomarker and will be evaluated in QBE Step 2.

Step 2: Identifying a Dichotomizing Threshold

We used a Monte-Carlo 2-fold cross-validation procedure to identify a threshold that minimizes the p value of the biomarker×treatment interaction. Specifically, for 100 iterations, we randomly selected half of the cases, balancing for treatment arm and pCR status, as our training set. We considered every value between the $10^{th}$ and $90^{th}$ percentile as a potential threshold to dichotomize the training set into "High" vs. "Low" RAB5A expressing groups; and fit a series of logistic regression models to assess the biomarker× treatment interaction (Model 1C). We selected the threshold that minimizes the LR test p value for the interaction term

|  | TDM1 (n = 52) | | TH (n = 31) | | Biomarker × Treatment Interaction (n = 83) | | | |
|---|---|---|---|---|---|---|---|---|
|  | | | | | Model 1C | | Model 1D | |
|  | Model 1A | | Model 1B | | Int_Co ef | Int_LR p | Int_Coef_HR Adj | Int_LRp_HR Adj |
|  | Coef | LRp | Coef | LRp | | | | |
| HSP90AA1 | 0.23 | 0.57 | 0.82 | 0.29 | −0.59 | 0.51 | −0.75 | 0.44 |
| RAB11A | 0.11 | 0.83 | 0.12 | 0.88 | −0.01 | 0.99 | 0.01 | 1.00 |
| RAIMA | 0.78 | 0.17 | −0.06 | 0.94 | 0.83 | 0.39 | 0.81 | 0.41 |
| RAB5A | 2.39 | 0.01 | −1.93 | 0.24 | 4.32 | 0.02 | 4.30 | 0.03 | in the training set, use it to dichotomize the test set, and assess the significance of the biomarker×treatment interaction in the test set. We then combine the LR p values across the 100 test sets using the logit method; and the threshold yielding the minimum combined LR test p value was selected.

Figure 9:
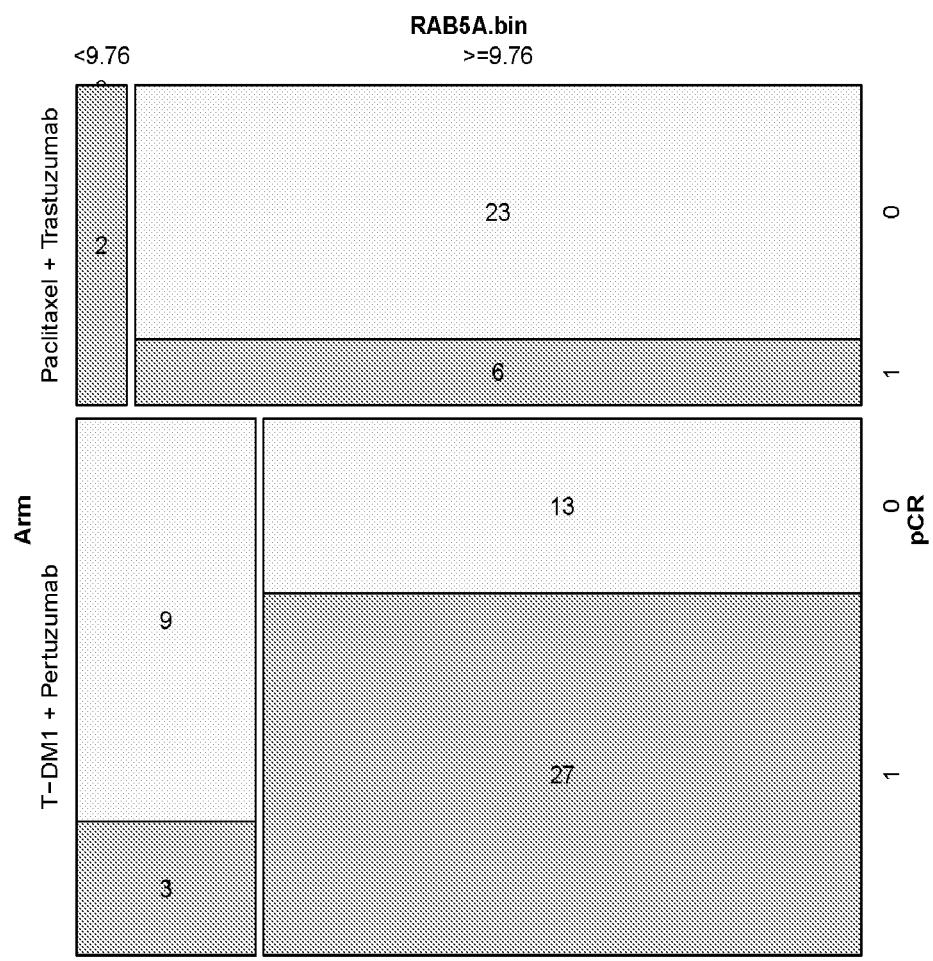
FIG. 9: Results of Monte-Carlo 2-fold cross-validation procedure to identify a threshold that minimizes the p value of the biomarker×treatment interaction.

Using this procedure, a threshold of 9.76 was selected. See FIG. 9. As a dichotomous variable, having high RAB5A level also associates with response in the TDM1+P (OR=5.99 (95% CI: 1.23-40.27), Fisher's Exact test p=0.01) but not the control arm (OR: 0 (95% CI: 0~1.74), Fisher's Exact test p=0.06); and have a biomarker×treatment interaction term with LR p=0.001.

Although 9.76 was the optimal threshold identified by this procedure, only 2 patients in the TH arm have RAB5A levels <9.76. This may in part be attributed to the difference in RAB5A expression in the TH and the TDM1+P arm, where the RAB5A levels are significantly higher in the TH arm than the TDM1+P arm. Array design may contribute to this difference. We may wish to consider evaluating biomarker performance within the TDM1+P arm alone (rather than using models that assess biomarker×treatment interactions as was pre-specified in the analysis plan). Using a Monte Carlo procedure similar to the one described above (but fitting model 1A in the TDM1+P alone), the optimal threshold that would be selected remains 9.76.

Figure 10:
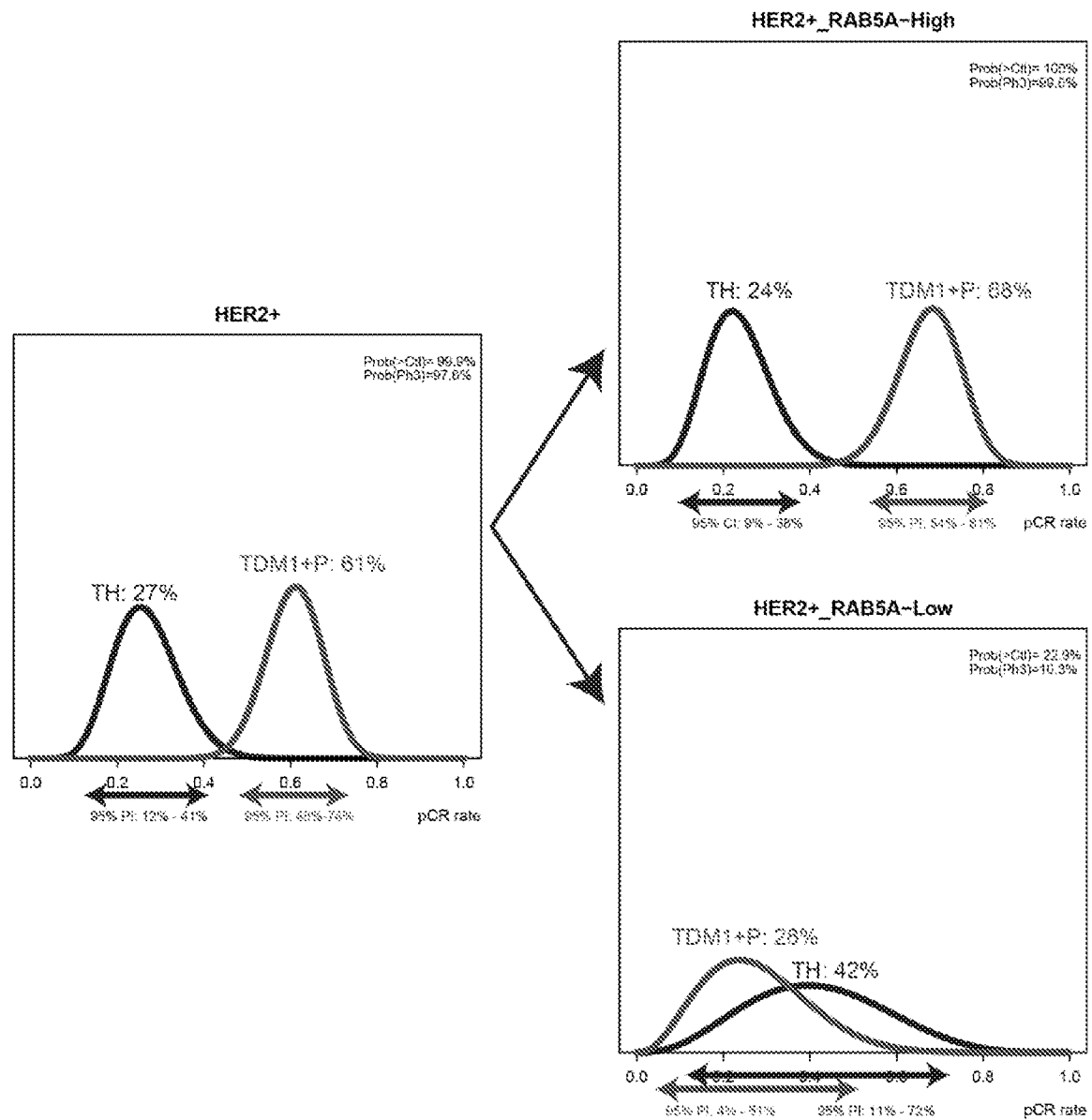
FIG. 10: Bayesian pCR probability curves related to RAB5A expression.

Step 3: Bayesian Estimated pCR Rates within RAB5A Groups in the Context of the HER2+Graduating Signature Model 2: pCR HR+RAB5A+Treatment+HR×Treatment+RAB5A×Treatment When we applied the optimal threshold identified (9.76) to dichotomize patients into RAB5A-High (>=9.76) and RAB5A-Low (<9.76) groups, the Bayesian estimated pCR probability is 68% in the TDM1+P arm relative to 24% in the control arm in the RAB5A-High patients. In contrast, the estimated pCR probability is 28% in the RAB5A-Low subset in the TDM1+P arm and 42% in the TH arm. For comparison, using the same model, the estimated pCR probability of the entire HER2+ group is 61% in the TDM1+P arm and 27% in the TH arm. The Bayesian pCR probability curves are shown in FIG. 10.

Example 3

This example shows the valuation of correlation between HSP90, Rab11a, Rab4A and Rab5a expression profile and treatment outcome for the TH- and T-DM1+P arm in the 1-SPY2 study. The RNA expression profile from the 1-SPY-2 data was evaluated for correlation between pCR and the expression level of HSP90, Rab11A, Rab4A and Rab5a in the two treatment arms receiving T-Trastuzumab+Chemotherapy (TH) or Trastuzumab-emtasin+Pertuzumab+Chemotherapy (TDM1+P). There is a significant difference in Rab5A expression levels between the pCR 0 and pCR 1 group in the T-DM1+P arm. No significant difference in found for any of the other proteins in any of the two arms.

| Trastuzumab + Chemotherapy (TH) | | | |
|---|---|---|---|
| | pCR = 0 (progressive disease) | pCR = 1 (complete response) | P value (t-test) |
| HSP90 | 12.84665 | 13.08863 | 0.322 |
| Rab 11A | 9.695248 | 9.7273 | 0.884 |
| Rab 4A | 9.641496 | 9.624925 | 0.942 |
| Rab 5A | 10.21211 | 10.08929 | 0.262 |

| Trastuzumab-emtasin + Pertuzumab + Chemotherapy | | | |
|---|---|---|---|
| | pCR = 0 (progressive disease) | pCR = 1 (complete response) | P value (t-test) |
| HSP90 | 12.75205 | 12.86073 | 0.584 |
| Rab 11A | 9.614195 | 9.645913 | 0.834 |
| Rab 4A | 9.3083 | 9.502127 | 0.181 |
| Rab 5A | 9.852223 | 10.07459 | 0.015 |

REFERENCE LIST

1. A. de Gramont, S. Watson, L. M. Ellis, J. Rodon, J. Tabernero, A. de Gramont and S. R. Hamilton, *Nature reviews. Clinical oncology*, 2015, 12, 197-212.
2. D. J. Slamon, W. Godolphin, L. A. Jones, J. A. Holt, S. G. Wong, D. E. Keith, W. J. Levin, S. G. Stuart, J. Udove, A. Ullrich and et al., *Science*, 1989, 244, 707-712.
3. A. Hernandez-Blanquisett, D. Touya, K. Strasser-Weippl, R. Ruiz, J. St Louis and P. Goss, *Breast* (Edinburgh, Scotland), 2016, 29, 170-177.
4. M. F. Rimawi, R. Schiff and C. K. Osborne, *Annual review of medicine*, 2015, 66, 111-128.
5. R. A. Clynes, T. L. Towers, L. G. Presta and J. V. Ravetch, *Nature medicine*, 2000, 6, 443-446.
6. N. Harbeck, M. W. Beckmann, A. Rody, A. Schneeweiss, V. Muller, T. Fehm, N. Marschner, O. Gluz, I. Schrader, G. Heinrich, M. Untch and C. Jackisch, *Breast care* (Basel, Switzerland), 2013, 8, 49-55.
7. G. D. Lewis Phillips, G. Li, D. L. Dugger, L. M. Crocker, K. L. Parsons, E. Mai, W. A. Blattler, J. M. Lambert, R. V. Chari, R. J. Lutz, W. L. Wong, F. S. Jacobson, H. Koeppen, R. H. Schwall, S. R. Kenkare-Mitra, S. D. Spencer and M. X. Sliwkowski, *Cancer research*, 2008, 68, 9280-9290.
8. S. Verma, D. Miles, L. Gianni, I. E. Krop, M. Welslau, J. Baselga, M. Pegram, D. Y. Oh, V. Dieras, E. Guardino, L. Fang, M. W. Lu, S. Olsen and K. Blackwell, *The New England journal of medicine*, 2012, 367, 1783-1791.
9. J. M. Baron, B. L. Boster and C. M. Barnett, *Journal of oncology pharmacy practice: official publication of the International Society of Oncology Pharmacy Practitioners*, 2015, 21, 132-142.
10. H. K. Erickson, P. U. Park, W. C. Widdison, Y. V. Kovtun, L. M. Garrett, K. Hoffman, R. J. Lutz, V. S. Goldmacher and W. A. Blattler, *Cancer research*, 2006, 66, 4426-4433.
11. M. T. Martinez, J. A. Perez-Fidalgo, P. Martin-Martorell, J. M. Cejalvo, V. Pons, B. Bermejo, M. Martin, J. Albanell and A. Lluch, *Critical reviews in oncology/hematology*, 2016, 97, 96-106.
12. Y. Cao, J. D. Marks, J. W. Marks, L. H. Cheung, S. Kim and M. G. Rosenblum, *Cancer Res.*, 2009, 69, 8987-8995.
13. Y. Cao, J. D. Marks, Q. Huang, S. I. Rudnick, C. Xiong, W. N. Hittelman, X. Wen, J. W. Marks, L. H. Cheung, K. Boland, C. Li, G. P. Adams and M. G. Rosenblum, *Mol. Cancer Ther.*, 2012, 11, 143-153.
14. F. Stirpe, S. Olsnes and A. Pihl, *J Biol. Chem.*, 1980, 255, 6947-6953.
15. M. Ritchie, L. Tchistiakova and N. Scott, mAbs, 2013, 5, 13-21.
16. J. Baselga, G. D. Lewis Phillips, S. Verma, J. Ro, J. Huober, A. E. Guardino, M. K. Samant, S. Olsen, S. L. de Haas and M. D. Pegram, *Clinical cancer research: an official journal of the American Association for Cancer Research*, 2016, 22, 3755-3763.

17. S. B. Kim, H. Wildiers, I. E. Krop, M. Smitt, R. Yu, S. Lysbet de Haas and A. Gonzalez-Martin, *Int J Cancer*, 2016, 139, 2336-2342.
18. H. Stenmark, *Nature reviews. Molecular cell biology*, 2009, 10, 513-525.
19. B. Bull-Hansen, Y. Cao, K. Berg, E. Skarpen, M. G. Rosenblum and A. Weyergang, *J. Control Release.*, 2014, 182C:58-66. doi: 10.1016/j.jconrel.2014.03.014, 58-66.
20. M. G. Rosenblum, W. A. Kohr, K. L. Beattie, W. G. Beattie, W. Marks, P. D. Toman and L. Cheung, *J Interferon Cytokine Res.*, 1995, 15, 547-555.
21. A. Weyergang, P. K. Selbo and K. Berg, *J. Control Release.*, 2006, 111, 165-173.
22. K. Subik, J. F. Lee, L. Baxter, T. Strzepek, D. Costello, P. Crowley, L. Xing, M. C. Hung, T. Bonfiglio, D. G. Hicks and P. Tang, *Breast Cancer* (Auckl.). 2010, %20; 4:35-41, 35-41.
23. R. L. Dillon, S. Chooniedass, A. Premsukh, G. P. Adams, J. Entwistle, G. C. MacDonald and J. Cizeau, *Journal of immunotherapy* (Hagerstown, Md.: 1997), 2016, 39, 117-126.
24. M. Zerial and H. McBride, *Nature reviews. Molecular cell biology*, 2001, 2, 107-117.
25. C. D. Austin, A. M. De Maziere, P. I. Pisacane, S. M. van Dijk, C. Eigenbrot, M. X. Sliwkowski, J. Klumperman and R. H. Scheller, *Molecular biology of the cell*, 2004, 15, 5268-5282.
26. J. Baselga, E. A. Perez, T. Pienkowski and R. Bell, *The oncologist*, 2006, 11 Suppl 1, 4-12.
27. J. Baselga, *Eur. J. Cancer*, 2001, 37 Suppl 4, S16-S22.
28. E. A. Perez, S. A. Hurvitz, L. C. Amler, K. E. Mundt, V. Ng, E. Guardino and L. Gianni, *Breast cancer research: BCR*, 2014, 16, R50.
29. A. Citri, K. B. Skaria and Y. Yarden, *Experimental cell research*, 2003, 284, 54-65.
30. B. D. Grant and J. G. Donaldson, *Nature reviews. Molecular cell biology*, 2009, 10, 597-608.
31. E. Frittoli, A. Palamidessi, P. Marighetti, S. Confalonieri, F. Bianchi, C. Malinverno, G. Mazzarol, G. Viale, I. Martin-Padura, M. Garre, D. Parazzoli, V. Mattei, S. Cortellino, G. Bertalot, P. P. Di Fiore and G. Scita, *The Journal of cell biology*, 2014, 206, 307-328.
32. V. Bertelsen and E. Stang, *Membranes*, 2014, 4, 424-446.
33. K. Cortese, M. T. Howes, R. Lundmark, E. Tagliatti, P. Bagnato, A. Petrelli, M. Bono, H. T. McMahon, R. G. Parton and C. Tacchetti, *Molecular biology of the cell*, 2013, 24, 129-144.
34. S. Takahashi, K. Kubo, S. Waguri, A. Yabashi, H. W. Shin, Y. Katoh and K. Nakayama, *Journal of cell science*, 2012, 125, 4049-4057.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. Method of treating cancer in a subject:
comprising administering an effective amount of an immunoconjugate to the subject,
wherein the subject has been diagnosed as eligible for treatment with the immunoconjugate targeting a surface antigen expressed on the cancer cells when the measured expression level of Ras associated binding (RAB) protein 5 (RAB5), in the subject's cancer cell sample is increased as compared to a dichotomizing threshold,
wherein the expression level of RAB5 in cancer cells in a cell sample obtained from the subject has been measured, wherein said measuring has been performed by an in vitro assay, and the expression level has been compared to the dichotomizing threshold;
wherein the immunoconjugate is an antigen binding protein that is linked or joined to a drug or toxin, wherein the antigen-binding protein is an antibody, or an antigen-binding fragment thereof, or a protein ligand that binds to the cell surface antigen
and
wherein the surface antigen is a surface antigen internalized by a pathway for endocytosis, wherein said pathway comprises RAB5.

2. The method of claim 1, wherein the expression level of RAB5 in the cancer cells has been measured by measuring the level of RAB5 mRNA or RAB5 protein.

3. The method of claim 1, wherein the RAB5 is RAB5A, RAB5B or RAB5C.

4. The method of claim 1, further comprising measuring the expression level of one or more of RAB4, RAB11 or heat shock protein (HSP) 90 in the cancer cells in the cell sample obtained from the subject and optionally, wherein the expression level of one or more of RAB4, RAB11 or HSP90 has been incorporated into an expression index with the RAB5 expression level and the subject has been diagnosed as eligible for treatment with the immunoconjugate when the expression index is increased as compared to the dichotomizing threshold.

5. The method of claim 1, wherein the cancer cells are cancer cells that have been obtained from a surgical tumor sample, a biopsy sample or a blood sample.

6. The method of claim 1, wherein the surface antigen is selected from the group consisting of human epidermal growth factor receptor (HER)1, HER2, HER3, cluster of differentiation (CD)3ε, CD19, CD22, CD25, CD30, CD33, CD56, CEA (CD66e), CD74, CD79a, CD138, sodium-dependent phosphate transport protein 2b (NaPi2b), glycoprotein nonmetastatic melanoma protein B (gpNMB), trophoblast cell-surface antigen (TROP)-2, guanylate cyclase 2C (GUCY2C), Nectin-4, six-transmembrane epithelial antigen of prostate 1 (STEAP1), folate receptor α (FRα), interleukin (IL)-2R, epithelial cellular adhesion molecule (EpCAM), and mesothelin (MSLN).

7. The method of claim 1, wherein the immunoconjugate is selected from the group consisting of trastuzumab emtansine, brentuximab vedotin, inotuzumab ozogamicin, pinatuzumab vedotin, polatuzumab vedotin, lifastuzumab vedotin, glembatumumab vedotin, coltuximab ravtansine), lorvotuzumab mertansine, indatuximab ravtansine, sacitizumab govitican, labetuzumab govitican, milatuzumab doxorubicin, indusatumab vedotin, vadastuximab talirine, denintuzumab mafodotin, enfortumab vedotin, rovalpituzumab tesirine, vandortuzumab vedotin, mirvetuximab soravtansine, ABT-414, IMGN289, AMG595, MH3-B1/rGel, denileukin diftitox, moxetumomab pasudotox, oportuzumab monotox, resimmune, LMB-2, DT2219ARL, HuM195/rGel, RG7787, MOC31PE and D2C7-IT.

8. The method of claim 1, wherein the cancer cells are selected from the group consisting of breast cancer cells, colorectal cancer cells, lung cancer cells, prostate cancer cells, melanoma cells, glioblastoma cells, pancreatic cancer cells, renal cell carcinoma cells, ovarian cancer cells, bladder cancer cells, endometrial cancer cells, gastrointestinal cancer cells, mesothelioma cells, multiple myeloma cells, acute myelogenous leukemia cells, acute lymphoblastic leukemia cells, and Non-Hodgkin's Lymphoma.

9. The method of claim 1, wherein the expression of the surface antigen on the cancer cells of the cell sample obtained from the subject has been assayed.

10. The method of claim 1, wherein the protein ligand that binds to the cell surface antigen is EGF.

11. The method of claim 1, wherein the cancer cells are breast cancer cells.

12. The method of claim 11, wherein the surface antigen is selected from the group consisting of HER1, HER2, HER3, and the immunoconjugate is selected from the group consisting of trastuzumab emtansine (T-DM1), ABT-414, IMGN289, AMG595 and combinations thereof, and the immunoconjugate is targeting said surface antigen.

13. The method of claim 12, wherein the surface antigen is HER2.

14. The method of claim 13, wherein the immunoconjugate is Trastuzumab emtansine (T-DM1).

\* \* \* \* \*